United States Patent [19]
Izu et al.

[11] Patent Number: 5,710,016
[45] Date of Patent: Jan. 20, 1998

[54] ALMOND N-GLYCOSIDASE GENE

[75] Inventors: Hiroyuki Izu, Kyoto; Masanori Mitta, Kyoto-fu; Ikunoshin Kato, Uji, all of Japan

[73] Assignee: Takara Shuzo Co., Ltd., Kyoto-fu, Japan

[21] Appl. No.: 419,009

[22] Filed: Apr. 7, 1995

[30] Foreign Application Priority Data

Apr. 7, 1994 [JP] Japan .................................. 6-069283

[51] Int. Cl.⁶ ........................... C12N 15/29; C12N 15/52
[52] U.S. Cl. .................. 435/69.1; 435/320.1; 536/23.2; 536/23.6
[58] Field of Search .............................. 435/6, 195, 212, 435/219, 240.2, 252.3, 254.11, 254.2, 320.1, 69.1, 200; 536/23.2, 23.6

[56] References Cited

PUBLICATIONS

Lee et al, "Generation of cDNA Probes Directed by Amino Acid Sequence:Cloning of Urate Oxidase", Science, vol. 239, pp. 1288–1291, Mar. 11, 1988.

Mathews et al., "Mass Spectrometrically Derived Amino Acid Sequence of Thioredoxin from Chlorobium, an Evolutionarily Prominent Photosynthetic Bacterium," Journal Of Biological Chemistry, vol. 262, No. 16, pp. 7537–7545, Jun. 5, 1987.

Kaliberda et al. "Isolation of a glycopeptidase from sweet almond and determination of the N-terminal sequence of its protein moiety." Chemical Abstracts, vol. 113, No. 25, Abstract No. 226781 (Dec. 1990).

Beketaeva et al., "Preparation of nutrient yeast biomass using vegetable crude—involves adding beta–glucosidase to nutrient medium, hydrolosis of vegetable matter, and growing yeast on hydrolysate." Derwent Publications Ltd., abstract (Apr. 1992).

"Secretory preparation of animal protein—by culturing Schizosaccharomyces pombe which retains DNA at 3'-terminal of promoter region." Derwent Publications Ltd., abstract (Jul. 1991).

Kaliberda et al. "Deglycoylation of glycoproteins with glycopeptidamidase A." Chemical Abstracts, vol. 118, No. 13, Abstract No. 119557 (1992).

Takahashi, N.; "Demonstration of a New Amidase Acting On Glycopeptides"; Biochem. & Biophys. Resear. Comm., vol. 76, No. 4, pp. 1194–1207 (1977).

Takahashi, N. et al.; "Almond Glycopeptidase Acting On Aspartylglycosylamine Linkages", Biochimica et Biophysica Acta, Vo.. 657, pp. 457–467 (1981).

Tarentino A.L, et al.; "Oligosaccharide Accessibility To Peptide:N–Glycosidase As Promoted By Protein–Unfolding Reagents"; J. Biol. Chem., VO. 257, No. 18, pp. 10776–10780 (1982).

Taga, E.M., et al.; "Structural and Chemical Characterization Of A Homogeneous Peptide N–Glycosidase From Almond"; Biochem., Vo. 23, pp. 815–822 (1984).

Kaliberda, E.N., et al.; "Isolation Of Glycopeptidese From Sweet Almond And Determination Of The Amino–Terminal Sequence Of Its Protein Moiety"; Bio. Khimiya, vol. 16, No. 6 pp. 751–758 (1990) together with English Abstract Dialog.

Barsomian, G.D., et al.; "Cloning And Expression Of Peptide–N4–(N–acetyl–B–D–glucosaminyl)asparagine Amidase in Escherichia Coli"; J. Bio. Chem., vol. 265, No. 12, pp. 6967–6972 (1990).

Lemp, D. et al.; "Molecular Cloning And Heterologous Expression of N–Glycosidase F From Flavobacterium Meningosepticum"; J. Bio. Chem., vol. 265, No. 26, pp. 15606–15610 (1990).

Primary Examiner—Keith C. Furman
Attorney, Agent, or Firm—Browdy and Neimark

[57] ABSTRACT

An almond N-glycosidase gene and genes associated therewith are described. Vectors integrated such genes therein, recombinant microorganisms transformed with said vectors, and a process for preparing the almond N-glycosidase using said recombinant microorganisms are also described.

14 Claims, 3 Drawing Sheets

5,710,016

SEQUENCE LISTING ( 1 ) GENERAL INFORMATION:

( i i i ) NUMBER OF SEQUENCES: 43

( 2 ) INFORMATION FOR SEQ ID NO: 1:

( i ) SEQUENCE CHARACTERISTICS:
        ( A ) LENGTH: 571
        ( B ) TYPE: amino acid
        ( D ) TOPOLOGY: linear ( i i ) MOLECULE TYPE: peptide ( i x ) FEATURE:
        ( D ) OTHER INFORMATION: Xaa at position 27 is Pro or Ser.
            Xaa at position 74 is Arg or Gly.
        ( D ) OTHER INFORMATION: Xaa at position 152 is Lys or Glu.
            Xaa at position 179 is Ile pr Val.
        ( D ) OTHER INFORMATION: Xaa at position 488 is Arg or Gln.
            Xaa at position 506 is Glu or Gly.
        ( D ) OTHER INFORMATION: Xaa at position 511 is Ile or Val.

( x i ) SEQUENCE DESCRIPTION: SEQ ID NO: 1:

```
Glu Pro Thr Pro Leu His Asp Thr Pro Pro Thr Val Phe Phe Glu
 1               5                  10                 15

Val Thr Lys Pro Ile Glu Val Pro Lys Thr Lys Xaa Cys Ser Gln
                20                  25                 30

Leu Ile Leu Gln His Asp Phe Ala Tyr Thr Tyr Gly Gln Ala Pro
                35                  40                 45

Val Phe Ala Asn Tyr Thr Pro Pro Ser Asp Cys Pro Ser Gln Thr
                50                  55                 60

Phe Ser Thr Ile Val Leu Glu Trp Lys Ala Thr Cys Arg Xaa Arg
                65                  70                 75

Gln Phe Asp Arg Ile Phe Gly Val Trp Leu Gly Gly Val Glu Ile
                80                  85                 90

Leu Arg Ser Cys Thr Ala Glu Pro Arg Pro Asn Gly Ile Val Trp
                95                  100                105

Thr Val Glu Lys Asp Ile Thr Arg Tyr Tyr Ser Leu Leu Lys Ser
                110                 115                120

Asn Gln Thr Leu Ala Val Tyr Leu Gly Asn Leu Ile Asp Lys Thr
                125                 130                135

Tyr Thr Gly Ile Tyr His Val Asn Ile Ser Leu His Phe Tyr Pro
                140                 145                150

Ala Xaa Glu Lys Leu Asn Ser Phe Gln Gln Lys Leu Asp Asn Leu
                155                 160                165

Ala Ser Gly Tyr His Ser Trp Ala Asp Leu Ile Leu Pro Xaa Ser
                170                 175                180

Arg Asn Leu Pro Leu Asn Asp Gly Leu Trp Phe Glu Val Gln Asn
                185                 190                195

Ser Asn Asp Thr Glu Leu Lys Glu Phe Lys Ile Pro Gln Asn Ala
                200                 205                210

Tyr Arg Ala Val Leu Glu Val Tyr Val Ser Phe His Glu Asn Asp
                215                 220                225

Glu Phe Trp Tyr Ser Asn Leu Pro Asn Glu Tyr Ile Ala Ala Asn
                230                 235                240

Asn Leu Ser Gly Thr Pro Gly Asn Gly Pro Phe Arg Glu Val Val
                245                 250                255

Val Ser Leu Asp Gly Glu Val Val Gly Ala Val Trp Pro Phe Thr
                260                 265                270

Val Ile Phe Thr Gly Gly Ile Asn Pro Leu Leu Trp Arg Pro Ile
                275                 280                285

Thr Ala Ile Gly Ser Phe Asp Leu Pro Thr Tyr Asp Ile Glu Ile
                290                 295                300

Thr Pro Phe Leu Gly Lys Ile Leu Asp Gly Lys Ser His Lys Phe
                305                 310                315

Gly Phe Asn Val Thr Asn Ala Leu Asn Val Trp Tyr Val Asp Ala
                320                 325                330

Asn Leu His Leu Trp Leu Asp Lys Gln Ser Thr Lys Thr Glu Gly
                335                 340                345

Lys Leu Ser Lys His Ser Ser Leu Pro Leu Val Val Ser Leu Val
                350                 355                360

Ser Asp Phe Lys Gly Leu Asn Gly Thr Phe Leu Thr Arg Thr Ser
                365                 370                375

Arg Ser Val Ser Ser Thr Gly Trp Val Lys Ser Ser Tyr Gly Asn
                380                 385                390
```

|   |   |   |   |   |   |   |   |   |   |   |   |   |   |   |
|---|---|---|---|---|---|---|---|---|---|---|---|---|---|---|
| Ile | Thr | Thr | Arg | Ser<br>395 | Ile | Gln | Asp | Phe | Tyr<br>400 | Tyr | Ser | Asn | Ser | Met<br>405 |
| Val | Leu | Gly | Lys | Asp<br>410 | Gly | Asn | Met | Gln | Ile<br>415 | Val | Asn | Gln | Lys | Ile<br>420 |
| Ile | Phe | Asn | Asp | Ser<br>425 | Val | Tyr | Ile | Asn | Leu<br>430 | Pro | Ser | Ser | Tyr | Val<br>435 |
| His | Ser | Leu | Thr | Ser<br>440 | His | Lys | Thr | Phe | Pro<br>445 | Leu | Tyr | Leu | Tyr | Thr<br>450 |
| Asp | Phe | Leu | Gly | Gln<br>455 | Gly | Asn | Gly | Thr | Tyr<br>460 | Leu | Leu | Ile | Thr | Asn<br>465 |
| Val | Asp | Leu | Gly | Phe<br>470 | Ile | Glu | Lys | Lys | Ser<br>475 | Gly | Leu | Gly | Phe | Ser<br>480 |
| Asn | Ser | Ser | Leu | Arg<br>485 | Asn | Leu | Xaa | Ser | Ala<br>490 | Glu | Gly | Asn | Met | Val<br>495 |
| Val | Lys | Asn | Asn | Leu<br>500 | Val | Val | Ser | Gly | Leu<br>505 | Xaa | Ser | Thr | Gln | Gln<br>510 |
| Xaa | Tyr | Arg | Tyr | Asp<br>515 | Gly | Gly | Lys | Phe | Cys<br>520 | Tyr | Phe | Arg | Asn | Ile<br>525 |
| Ser | Ser | Ser | Asn | Tyr<br>530 | Thr | Ile | Leu | Tyr | Asp<br>535 | Lys | Val | Gly | Ser | Lys<br>540 |
| Cys | Asn | Lys | Lys | Ser<br>545 | Leu | Ser | Asn | Leu | Asp<br>550 | Phe | Val | Leu | Ser | Arg<br>555 |
| Leu | Trp | Pro | Phe | Gly<br>560 | Ala | Arg | Met | Asn | Phe<br>565 | Ala | Gly | Leu | Arg | Phe<br>570 |

Thr ( 2 ) INFORMATION FOR SEQ ID NO: 2:

( i ) SEQUENCE CHARACTERISTICS:
        ( A ) LENGTH: 1713
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 2:

```
GARCCNACNC  CN Y TNCA Y GA  Y ACNCCNCCN  ACNGTATTTT  TTGAAGTCAC  CAAACCCATT   60
GAAGTACCAA  AAACCAAG Y C  GTGTTCCCAG  CTCATTCTCC  AGCATGACTT  TGCCTACACA  120
TATGGCCAAG  CTCCAGTCTT  TGCAAACTAC  ACCCCTCCTT  CCGATTGCCC  ATCTCAAACT  180
TTCTCCACAA  TTGTCCTTGA  ATGGAAAGCT  ACCTGCAGAR  GAAGGCAATT  TGACCGCATT  240
TTCGGGGTTT  GGCTTGGTGG  GGTTGAGATT  CTCAGGAGCT  GCACAGCAGA  ACCAAGGCCT  300
AATGGGATTG  TTTGGACTGT  CGAGAAGGAC  ATCACAAGGT  ACTATTCACT  GCTTAAGAGT  360
AATCAAACAC  TTGCTGTTTA  TCTTGGCAAT  TTGATAGATA  AACCTACAC  TGGGATTTAT  420
CATGTGAATA  TAAGCCTTCA  TTTTTACCCT  GCTRAAGAGA  AATTGAATTC  TTTTCAGCAA  480
AAGTTGGATA  ATTTGGCATC  TGGGTACCAT  TCTTGGGCTG  ATTTGATTTT  ACCCRTTTCG  540
AGAAATCTSC  C Y TTGAATGA  Y GGGTTGTGG  TTTGAAGTTC  AGAATTCAAA  TGATACGGAA  600
TTGAAGGAGT  TCAAGATTCC  ACAAAATGCT  TATAGGGCTG  TGTTGGAGGT  GTATGTTTCA  660
TTTCACGAGA  ATGATGAATT  TTGGTATTCA  AATCTTCCTA  ATGAGTACAT  AGCTGCAAAC  720
AACCTTAGCG  GTACACC Y GG  AAATGGGCCT  TTTAGGGAGG  TTGTGGTCAG  TCTAGATGGT  780
GAGGTTGTTG  GTGCAGTCTG  GCCTTTTACT  GTGATTTTCA  CTGGAGGGAT  CAATCCTCTT  840
TTATGGAGAC  CAATTACTGC  AATTGGCTCA  TTCGATCTTC  CGACTTATGA  TATCGAAATT  900
```

```
ACACCATTTT TAGGGAAGAT ATTAGATGGG AAGAGCCACA AGTTCGGGTT TAATGTTACA    960
AATGCCTTAA ATGTTTGGTA CGTTGATGCA AATTTGCATC TTTGGTTGGA CAAACAGAGC   1020
ACAAAAACTG AAGGAAAGCT TTCGAAACAT AGTAGCTTGC CCCTTGTTGT TTCCCTGGTT   1080
TCAGATTTCA AGGGTTTAAA TGGSACATTT TTGACAAGGA CAAGCAGGTC CGTGTCATCM   1140
ACTGGATGGG TGAAGTCTTC CTATGGGAAT ATCACAACCC GTTCAATTCA AGACTTCTAT   1200
TACAGTAATT CAATGGTCCT GGGGAAAGAT GGTAATATGC AGATAGTCAA CCAGAAGATC   1260
ATTTTCAATG ACTCAGTTTA TATTAACCTG CCATCCTCCT ATGTTCACTC ACTGACATCA   1320
CACAAAACAT TTCCACTTTA TTTGTACACT GACTTCTTAG GACAAGGAAA TGGAACTTAT   1380
TTATTGATTA CAAATGTGGA CTTGGGATTT ATTGAGAAGA AGTCTGGTTT GGGWTTCTCG   1440
AACAGCTCTC TCAGAAATCT GCRGAGTGCT GAGGGCAATA TGGTTGTGAA AACAATTTG    1500
GTTGTGAGTG GATTGGRGAG CAC Y CAGCAA RTCTATAGAT ATGATGGTGG TAAATTCTGT  1560
TACTTCAGAA ATATAAGCAG CTCAAACTAC ACAATACTCT ATGACAAGGT GGGGAGCAAA   1620
TGCAACAAAA AATCGTTGTC TAATTTGGAT TTTGTCTTAA GCAGACTGTG GCCTTTTGGT   1680
GCTCGAATGA ATTTTGCTGG TCTCCGATTT ACA                                1713
```

(2) INFORMATION FOR SEQ ID NO: 3:

(i) SEQUENCE CHARACTERISTICS:
        (A) LENGTH: 10
        (B) TYPE: amino acid
        (D) TOPOLOGY: linear (ii) MOLECULE TYPE: peptide (v) FRAGMENT TYPE: N-terminal fragment (xi) SEQUENCE DESCRIPTION: SEQ ID NO: 3:

```
Ile Asp Pro Arg Val Val Xaa Ala Xaa Leu
 1               5                   10
```

(2) INFORMATION FOR SEQ ID NO: 4:

(i) SEQUENCE CHARACTERISTICS:
        (A) LENGTH: 20
        (B) TYPE: amino acid
        (D) TOPOLOGY: linear (ii) MOLECULE TYPE: peptide (xi) SEQUENCE DESCRIPTION: SEQ ID NO: 4:

```
Leu Ala Ser Gly Tyr His Ser Trp Ala Asp Leu Ile Leu Pro Ile
 1               5                   10                  15
Ser Arg Asn Leu Pro
                20
```

(2) INFORMATION FOR SEQ ID NO: 5:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: other nucleic acid (synthesized DNA)

(xi) SEQUENCE DESCRIPTION: SEQ ID NO: 5:

```
WSNGGNTA Y C  A YWSNTGGGC    20
```

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (synthesized DNA)

( x i ) SEQUENCE DESCRIPTION: SEQ ID NO: 6:

TGGGCNGAY Y TNATH YTNCC     20

( 2 ) INFORMATION FOR SEQ ID NO: 7:

( i ) SEQUENCE CHARACTERISTICS:
        ( A ) LENGTH: 21
        ( B ) TYPE: amino acid
        ( D ) TOPOLOGY: linear ( i i ) MOLECULE TYPE: peptide ( x i ) SEQUENCE DESCRIPTION: SEQ ID NO: 7:

Asn Asn Leu Val Val Ser Gly Leu Gly Ser Thr Gln Gln Val Tyr
 1                  5                       10                   15

Arg Tyr Asp Gly Gly Lys
20

( 2 ) INFORMATION FOR SEQ ID NO: 8:

( i ) SEQUENCE CHARACTERISTICS:
        ( A ) LENGTH: 18
        ( B ) TYPE: amino acid
        ( D ) TOPOLOGY: linear ( i i ) MOLECULE TYPE: peptide ( x i ) SEQUENCE DESCRIPTION: SEQ ID NO: 8:

Phe Xaa Tyr Phe Arg Xaa Ile Ser Ser Ser Xaa Tyr Thr Ile Leu
 1                  5                       10                   15

Tyr Asp Lys ( 2 ) INFORMATION FOR SEQ ID NO: 9:

( i ) SEQUENCE CHARACTERISTICS:
        ( A ) LENGTH: 24
        ( B ) TYPE: amino acid
        ( D ) TOPOLOGY: linear ( i i ) MOLECULE TYPE: peptide ( x i ) SEQUENCE DESCRIPTION: SEQ ID NO: 9:

Ser Ser Tyr Gly Xaa Ile Thr Thr Arg Ser Ile Gln Asp Phe Tyr
 1                  5                       10                   15

Tyr Ser Asn Ser Met Val Leu Gly Lys
                 20

( 2 ) INFORMATION FOR SEQ ID NO: 10:

( i ) SEQUENCE CHARACTERISTICS:
        ( A ) LENGTH: 22
        ( B ) TYPE: amino acid
        ( D ) TOPOLOGY: linear ( i i ) MOLECULE TYPE: peptide ( x i ) SEQUENCE DESCRIPTION: SEQ ID NO: 10:

Ile Ile Phe Xaa Asp Ser Xaa Tyr Xaa Asn Leu Pro Ser Ser Tyr

```
Val His Xaa Leu Xaa Xaa His
              20
```

(2) INFORMATION FOR SEQ ID NO: 11:

(i) SEQUENCE CHARACTERISTICS:
        (A) LENGTH: 24
        (B) TYPE: amino acid
        (D) TOPOLOGY: linear (ii) MOLECULE TYPE: peptide (xi) SEQUENCE DESCRIPTION: SEQ ID NO: 11:

```
Phe Gly Phe Xaa Val Thr Asn Ala Leu Asn Val Trp Tyr Val Asp
 1           5                  10                      15
Ala Asn Leu His Leu Trp Leu Asp Lys
              20
```

(2) INFORMATION FOR SEQ ID NO: 12:

(i) SEQUENCE CHARACTERISTICS:
        (A) LENGTH: 22
        (B) TYPE: amino acid
        (D) TOPOLOGY: linear (ii) MOLECULE TYPE: peptide (xi) SEQUENCE DESCRIPTION: SEQ ID NO: 12:

```
Ser Gly Leu Gly Phe Ser Xaa Ser Ser Leu Arg Asn Leu Gln Ser
 1           5                  10                      15
Ala Glu Gly Asn Met Val Val
              20
```

(2) INFORMATION FOR SEQ ID NO: 13:

(i) SEQUENCE CHARACTERISTICS:
        (A) LENGTH: 20
        (B) TYPE: amino acid
        (D) TOPOLOGY: linear (ii) MOLECULE TYPE: peptide (xi) SEQUENCE DESCRIPTION: SEQ ID NO: 13:

```
Gly Leu Xaa Gly Thr Phe Leu Thr Arg Thr Ser Arg Ser Val Ser
 1           5                  10                      15
Xaa Thr Gly Xaa Val
              20
```

(2) INFORMATION FOR SEQ ID NO: 14:

(i) SEQUENCE CHARACTERISTICS:
        (A) LENGTH: 21
        (B) TYPE: amino acid
        (D) TOPOLOGY: linear (ii) MOLECULE TYPE: peptide (xi) SEQUENCE DESCRIPTION: SEQ ID NO: 14:

```
Thr Phe Pro Leu Tyr Leu Tyr Thr Xaa Phe Leu Gly Gln Gly Xaa
 1           5                  10                      15
Xaa Thr Xaa Leu Leu Ile
              20
```

(2) INFORMATION FOR SEQ ID NO: 15:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) MOLECULE TYPE: other nucleic acid (DNA)

( x i ) SEQUENCE DESCRIPTION: SEQ ID NO: 15:

CCRTCRTANC KRTANAC Y TG Y TG    23

( 2 ) INFORMATION FOR SEQ ID NO: 16:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 16:

TGNARRTTNG CRTCNACRTA CC    22

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 17:

GCRTTNGTNA CRTTRAANCC    20

( 2 ) INFORMATION FOR SEQ ID NO: 18:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 18:

GTTTCCCAG TCACGACTTT TTTTTTTTT TTTTTT    37

( 2 ) INFORMATION FOR SEQ ID NO: 19:

( i ) SEQUENCE CHARACTERISTICS:
        ( A ) LENGTH: 485
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 19:

```
TGG  GCT  GAT  TTG  ATT  TTA  CCC  GTT  TCG  AGA  AAT  CTG  CCC  TTG  AAT      45
Trp  Ala  Asp  Leu  Ile  Leu  Pro  Val  Ser  Arg  Asn  Leu  Pro  Leu  Asn
 1                   5                        10                       15

GAT  GGG  TTG  TGG  TTT  GAA  GTT  CAG  AAT  TCA  AAT  GAT  ACG  GAA  TTG      90
Asp  Gly  Leu  Trp  Phe  Glu  Val  Gln  Asn  Ser  Asn  Asp  Thr  Glu  Leu
                     20                       25                       30

AAG  GAG  TTC  AAG  ATT  CCA  CAA  AAT  GCT  TAT  AGG  GCT  GTG  TTG  GAG     135
Lys  Glu  Phe  Lys  Ile  Pro  Gln  Asn  Ala  Tyr  Arg  Ala  Val  Leu  Glu
```

```
               35                           40                           45
GTG  TAT  GTT  TCA  TTT  CAC  GAG  AAT  GAT  GAA  TTT  TGG  TAT  TCA  AAT        180
Val  Tyr  Val  Ser  Phe  His  Glu  Asn  Asp  Glu  Phe  Trp  Tyr  Ser  Asn
                    50                           55                           60

CTT  CCT  AAT  GAG  TAC  ATA  GCT  GCA  AAC  AAC  CTT  AGC  GGT  ACA  CCT        225
Leu  Pro  Asn  Glu  Tyr  Ile  Ala  Ala  Asn  Asn  Leu  Ser  Gly  Thr  Pro
                    65                           70                           75

GGA  AAT  GGG  CCT  TTT  AGG  GAG  GTT  GTG  GTC  AGT  CTA  GAT  GGT  GAG        270
Gly  Asn  Gly  Pro  Phe  Arg  Glu  Val  Val  Val  Ser  Leu  Asp  Gly  Glu
                    80                           85                           90

GTT  GTT  GGT  GCA  GTC  TGG  CCT  TTT  ACT  GTG  ATT  TTC  ACT  GGA  GGG        315
Val  Val  Gly  Ala  Val  Trp  Pro  Phe  Thr  Val  Ile  Phe  Thr  Gly  Gly
                    95                          100                          105

ATC  AAT  CCT  CTT  TTA  TGG  AGA  CCA  ATT  ACT  GCA  ATT  GGC  TCA  TTC        360
Ile  Asn  Pro  Leu  Leu  Trp  Arg  Pro  Ile  Thr  Ala  Ile  Gly  Ser  Phe
                   110                          115                          120

GAT  CTT  CCG  ACT  TAT  GAT  ATC  GAA  ATT  ACA  CCA  TTT  TTA  GGG  AAG        405
Asp  Leu  Pro  Thr  Tyr  Asp  Ile  Glu  Ile  Thr  Pro  Phe  Leu  Gly  Lys
                   125                          130                          135

ATA  TTA  GAT  GGG  ATG  AGC  CAC  AAG  TTC  GGG  TTT  AAT  GTT  ACA  AAT        450
Ile  Leu  Asp  Gly  Met  Ser  His  Lys  Phe  Gly  Phe  Asn  Val  Thr  Asn
                   140                          145                          150

GCC  TTA  AAT  GTT  TGG  TAC  GTC  GAC  GCT  AAT  CTG  CA                        485
Ala  Leu  Asn  Val  Trp  Tyr  Val  Asp  Ala  Asn  Leu
                   155                          160
```

( 2 ) INFORMATION FOR SEQ ID NO: 20:

( i ) SEQUENCE CHARACTERISTICS:
        ( A ) LENGTH: 485
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 20:

```
TGG  GCG  GAT  TTG  ATT  TTA  CCC  GTT  TCG  AGA  AAT  CTG  CCT  TTG  AAT         45
Trp  Ala  Asp  Leu  Ile  Leu  Pro  Val  Ser  Arg  Asn  Leu  Pro  Leu  Asn
 1                   5                           10                           15

GAT  GGG  TTG  TGG  TTT  GAA  GTT  CAG  AAT  TCA  AAT  GAT  ACG  GAA  TTG         90
Asp  Gly  Leu  Trp  Phe  Glu  Val  Gln  Asn  Ser  Asn  Asp  Thr  Glu  Leu
                    20                           25                           30

AAG  GAG  TTC  AAG  ATT  CCA  CAA  AAT  GCT  TAT  AGG  GCT  GTG  TTG  GAG        135
Lys  Glu  Phe  Lys  Ile  Pro  Gln  Asn  Ala  Tyr  Arg  Ala  Val  Leu  Glu
                    35                           40                           45

GTG  TAT  GTT  TCA  TTT  CAC  GAG  AAT  GAT  GAA  TTT  TGG  TAT  TCA  AAT        180
Val  Tyr  Val  Ser  Phe  His  Glu  Asn  Asp  Glu  Phe  Trp  Tyr  Ser  Asn
                    50                           55                           60

CTT  CCT  AAT  GAG  TAC  ATA  GCT  GCA  AAC  AAC  CTT  AGC  GGT  ACA  CCC        225
Leu  Pro  Asn  Glu  Tyr  Ile  Ala  Ala  Asn  Asn  Leu  Ser  Gly  Thr  Pro
                    65                           70                           75

GGA  AAT  GGG  CCT  TTT  AGG  GAG  GTT  GTG  GTC  AGT  CTA  GAT  GGT  GAG        270
Gly  Asn  Gly  Pro  Phe  Arg  Glu  Val  Val  Val  Ser  Leu  Asp  Gly  Glu
                    80                           85                           90

GTT  GTT  GGT  GCA  GTC  TGG  CCT  TTT  ACT  GTG  ATT  TTC  ACT  GGA  GGG        315
Val  Val  Gly  Ala  Val  Trp  Pro  Phe  Thr  Val  Ile  Phe  Thr  Gly  Gly
                    95                          100                          105

ATC  AAT  CCT  CTT  TTA  TGG  AGA  CCA  ATT  ACT  GCA  ATT  GGC  TCA  TTC        360
Ile  Asn  Pro  Leu  Leu  Trp  Arg  Pro  Ile  Thr  Ala  Ile  Gly  Ser  Phe
110                          115                          120

GAT  CTT  CCG  ACT  TAT  GAT  ATC  GAA  ATT  ACA  CCA  TTT  TTA  GGG  AAG        405
```

| Asp | Leu | Pro | Thr | Tyr | Asp | Ile | Glu | Ile | Thr | Pro | Phe | Leu | Gly | Lys | |
|-----|-----|-----|-----|-----|-----|-----|-----|-----|-----|-----|-----|-----|-----|-----|---|
| 125 |     |     |     |     | 130 |     |     |     |     | 135 |     |     |     |     |   |

| ATA | TTA | GAT | GGG | AAG | AGC | CAC | AAG | TTC | GGG | TTT | AAT | GTT | ACA | AAT | 450 |
|-----|-----|-----|-----|-----|-----|-----|-----|-----|-----|-----|-----|-----|-----|-----|-----|
| Ile | Leu | Asp | Gly | Lys | Ser | His | Lys | Phe | Gly | Phe | Asn | Val | Thr | Asn |     |
| 140 |     |     |     |     | 145 |     |     |     |     | 150 |     |     |     |     |     |

| GCC | TTA | AAT | GTT | TGG | TAC | GTT | GAC | GCA | AAC | CTG | CA  | 485 |
|-----|-----|-----|-----|-----|-----|-----|-----|-----|-----|-----|-----|-----|
| Ala | Leu | Asn | Val | Trp | Tyr | Val | Asp | Ala | Asn | Leu |     |     |
| 155 |     |     |     |     | 160 |     |     |     |     |     |     |     |

( 2 ) INFORMATION FOR SEQ ID NO: 21:

( i ) SEQUENCE CHARACTERISTICS:
        ( A ) LENGTH: 485
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 21:

| TGG | GCT | GAT | TTG | ATT | TTG | CCC | ATT | TCG | AGA | AAT | CTG | CCT | TTG | AAT | 45 |
|-----|-----|-----|-----|-----|-----|-----|-----|-----|-----|-----|-----|-----|-----|-----|----|
| Trp | Ala | Asp | Leu | Ile | Leu | Pro | Ile | Ser | Arg | Asn | Leu | Pro | Leu | Asn |    |
| 1   |     |     |     | 5   |     |     |     |     | 10  |     |     |     |     | 15  |    |

| GAT | GGG | TTG | TGG | TTT | GAA | GTT | CAG | AAT | TCA | AAT | GAT | ACG | GAA | TTG | 90 |
|-----|-----|-----|-----|-----|-----|-----|-----|-----|-----|-----|-----|-----|-----|-----|----|
| Asp | Gly | Leu | Trp | Phe | Glu | Val | Gln | Asn | Ser | Asn | Asp | Thr | Glu | Leu |    |
|     |     |     |     | 20  |     |     |     |     | 25  |     |     |     |     | 30  |    |

| AAG | GAG | TTC | AAG | ATT | CCA | CAA | AAT | GCT | TAT | AGG | GCT | GTG | TTG | GAG | 135 |
|-----|-----|-----|-----|-----|-----|-----|-----|-----|-----|-----|-----|-----|-----|-----|-----|
| Lys | Glu | Phe | Lys | Ile | Pro | Gln | Asn | Ala | Tyr | Arg | Ala | Val | Leu | Glu |     |
|     |     |     |     | 35  |     |     |     |     | 40  |     |     |     |     | 45  |     |

| GTG | TAT | GTT | TCA | TTT | CAC | GAG | AAT | GAT | GAA | TTT | TGG | TAT | TCA | AAT | 180 |
|-----|-----|-----|-----|-----|-----|-----|-----|-----|-----|-----|-----|-----|-----|-----|-----|
| Val | Tyr | Val | Ser | Phe | His | Glu | Asn | Asp | Glu | Phe | Trp | Tyr | Ser | Asn |     |
|     |     |     |     | 50  |     |     |     |     | 55  |     |     |     |     | 60  |     |

| CTT | CCT | AAT | GAG | TAC | ATA | GCT | GCA | AAC | AAC | CTT | AGC | GGT | ACA | CCT | 225 |
|-----|-----|-----|-----|-----|-----|-----|-----|-----|-----|-----|-----|-----|-----|-----|-----|
| Leu | Pro | Asn | Glu | Tyr | Ile | Ala | Ala | Asn | Asn | Leu | Ser | Gly | Thr | Pro |     |
|     |     |     |     | 65  |     |     |     |     | 70  |     |     |     |     | 75  |     |

| GGA | AAT | GGG | CCT | TTT | AGG | GAG | GTT | GTG | GTC | AGT | CTA | GAT | GGT | GAG | 270 |
|-----|-----|-----|-----|-----|-----|-----|-----|-----|-----|-----|-----|-----|-----|-----|-----|
| Gly | Asn | Gly | Pro | Phe | Arg | Glu | Val | Val | Val | Ser | Leu | Asp | Gly | Glu |     |
|     |     |     |     | 80  |     |     |     |     | 85  |     |     |     |     | 90  |     |

| GTT | GTT | GGT | GCA | GTC | TGG | CCT | TTT | ACT | GTG | ATT | TTC | ACT | GGA | GGG | 315 |
|-----|-----|-----|-----|-----|-----|-----|-----|-----|-----|-----|-----|-----|-----|-----|-----|
| Val | Val | Gly | Ala | Val | Trp | Pro | Phe | Thr | Val | Ile | Phe | Thr | Gly | Gly |     |
|     |     |     |     | 95  |     |     |     |     | 100 |     |     |     |     | 105 |     |

| ATC | AAT | CCT | CTT | TTA | TGG | AGA | CCA | ATT | ACT | GCA | ATT | GGC | TCA | TTC | 360 |
|-----|-----|-----|-----|-----|-----|-----|-----|-----|-----|-----|-----|-----|-----|-----|-----|
| Ile | Asn | Pro | Leu | Leu | Trp | Arg | Pro | Ile | Thr | Ala | Ile | Gly | Ser | Phe |     |
|     |     |     |     | 110 |     |     |     |     | 115 |     |     |     |     | 120 |     |

| GAT | CTT | CCG | ACT | TAT | GAT | ATC | GAA | ATT | ACA | CCA | TTT | TTA | GGG | AAG | 405 |
|-----|-----|-----|-----|-----|-----|-----|-----|-----|-----|-----|-----|-----|-----|-----|-----|
| Asp | Leu | Pro | Thr | Tyr | Asp | Ile | Glu | Ile | Thr | Pro | Phe | Leu | Gly | Lys |     |
|     |     |     |     | 125 |     |     |     |     | 130 |     |     |     |     | 135 |     |

| ATA | TTA | GAT | GGG | AAG | AGC | CAC | AAG | TTC | GGG | TTT | AAT | GTT | ACA | AAT | 450 |
|-----|-----|-----|-----|-----|-----|-----|-----|-----|-----|-----|-----|-----|-----|-----|-----|
| Ile | Leu | Asp | Gly | Lys | Ser | His | Lys | Phe | Gly | Phe | Asn | Val | Thr | Asn |     |
|     |     |     |     | 140 |     |     |     |     | 145 |     |     |     |     | 150 |     |

| GCC | TTA | AAT | GTT | TGG | TAT | GTC | GAC | GCA | AAC | CTG | CA  | 485 |
|-----|-----|-----|-----|-----|-----|-----|-----|-----|-----|-----|-----|-----|
| Ala | Leu | Asn | Val | Trp | Tyr | Val | Asp | Ala | Asn | Leu |     |     |
|     |     |     |     | 155 |     |     |     |     | 160 |     |     |     |

( 2 ) INFORMATION FOR SEQ ID NO: 22:

( i ) SEQUENCE CHARACTERISTICS:
        ( A ) LENGTH: 485
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 22:

```
TGG GCG GAT TTG ATT TTA CCC ATT TCG AGA AAT CTC CCT TTG AAT      45
Trp Ala Asp Leu Ile Leu Pro Ile Ser Arg Asn Leu Pro Leu Asn
 1               5                  10                  15

GAT GGG TTG TGG TTT GAA GTT CAG AAT TCA AAT GAT ACG GAA TTG      90
Asp Gly Leu Trp Phe Glu Val Gln Asn Ser Asn Asp Thr Glu Leu
                20                  25                  30

AAG GAG TTC AAG ATT CCA CAA AAT GCT TAT AGG GCT GTG TTG GAG     135
Lys Glu Phe Lys Ile Pro Gln Asn Ala Tyr Arg Ala Val Leu Glu
                 35                  40                  45

GTG TAT GTT TCA TTT CAC GAG AAT GAT GAA TTT TGG TAT TCA AAT     180
Val Tyr Val Ser Phe His Glu Asn Asp Glu Phe Trp Tyr Ser Asn
                50                  55                  60

CTT CCT AAT GAG TAC ATA GCT GCA AAC AAC CTT AGC GGT ACA CCC     225
Leu Pro Asn Glu Tyr Ile Ala Ala Asn Asn Leu Ser Gly Thr Pro
                 65                  70                  75

GGA AAT GGG CCT TTT AGG GAG GTT GTG GTC AGT CTA GAT GGT GAG     270
Gly Asn Gly Pro Phe Arg Glu Val Val Val Ser Leu Asp Gly Glu
                 80                  85                  90

GTT GTT GGT GCA GTC TGG CCT TTT ACT GTG ATT TTC ACT GGA GGG     315
Val Val Gly Ala Val Trp Pro Phe Thr Val Ile Phe Thr Gly Gly
                 95                 100                 105

ATC AAT CCT CTT TTA TGG AGA CCA ATT ACT GCA ATT GGC TCA TTC     360
Ile Asn Pro Leu Leu Trp Arg Pro Ile Thr Ala Ile Gly Ser Phe
                110                 115                 120

GAT CTT CCG ACT TAT GAT ATC GAA ATT ACA CCA TTT TTA GGG AAG     405
Asp Leu Pro Thr Tyr Asp Ile Glu Ile Thr Pro Phe Leu Gly Lys
                125                 130                 135

ATA TTA GAT GGG AAG AGC CAC AAG TTC GGG TTT AAT GTT ACA AAT     450
Ile Leu Asp Gly Lys Ser His Lys Phe Gly Phe Asn Val Thr Asn
                140                 145                 150

GCC TTA AAT GTT TGG TAC GTC GAC GCG AAC CTG CA                  485
Ala Leu Asn Val Trp Tyr Val Asp Ala Asn Leu
                155                 160
```

( 2 ) INFORMATION FOR SEQ ID NO: 23:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) MOLECULE TYPE: other nucleic acid (DNA)

( x i ) SEQUENCE DESCRIPTION: SEQ ID NO: 23:

AAGTTCAGAA TTCAAATGAT ACGG      24

( 2 ) INFORMATION FOR SEQ ID NO: 24:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) MOLECULE TYPE: other nucleic acid (DNA)

( x i ) SEQUENCE DESCRIPTION: SEQ ID NO: 24:

TGTTGGAGGT GTATGTTTCA TTTCACG      27

( 2 ) INFORMATION FOR SEQ ID NO: 25:

( i ) SEQUENCE CHARACTERISTICS:
( A ) LENGTH: 17

(B) TYPE: nucleic acid
(C) STRANDEDNESS: single
(D) TOPOLOGY: linear (ii) MOLECULE TYPE: other nucleic acid (DNA)

(xi) SEQUENCE DESCRIPTION: SEQ ID NO: 25:

GTTTTCCCAG TCACGAC     17

(2) INFORMATION FOR SEQ ID NO: 26:

(i) SEQUENCE CHARACTERISTICS:
(A) LENGTH: 1435
(B) TYPE: nucleic acid
(C) STRANDEDNESS: double
(D) TOPOLOGY: linear (ii) MOLECULE TYPE: cDNA to mRNA (xi) SEQUENCE DESCRIPTION: SEQ ID NO: 26:

```
TG  TTG  GAG  GTG  TAT  GTT  TCA  TTT  CAC  GAG  AAT  GAT  GAA  TTT  TGG  TAT       47
    Leu  Glu  Val  Tyr  Val  Ser  Phe  His  Glu  Asn  Asp  Glu  Phe  Trp  Tyr
    1              5                        10                       15

TCA  AAT  CTT  CCT  AAT  GAG  TAC  ATA  GCT  GCA  AAC  AAC  CTT  AGC  GGT            92
Ser  Asn  Leu  Pro  Asn  Glu  Tyr  Ile  Ala  Ala  Asn  Asn  Leu  Ser  Gly
                    20                        25                       30

ACA  CCT  GGA  AAT  GGG  CCT  TTT  AGG  GAG  GTT  GTG  GTC  AGT  CTA  GAT           137
Thr  Pro  Gly  Asn  Gly  Pro  Phe  Arg  Glu  Val  Val  Val  Ser  Leu  Asp
                    35                        40                       45

GGT  GAG  GTT  GTT  GGT  GCA  GTC  TGG  CCT  TTT  ACT  GTG  ATT  TTC  ACT           182
Gly  Glu  Val  Val  Gly  Ala  Val  Trp  Pro  Phe  Thr  Val  Ile  Phe  Thr
                    50                        55                       60

GGA  GGG  ATC  AAT  CCT  CTT  TTA  TGG  AGA  CCA  ATT  ACT  GCA  ATT  GGC           227
Gly  Gly  Ile  Asn  Pro  Leu  Leu  Trp  Arg  Pro  Ile  Thr  Ala  Ile  Gly
                    65                        70                       75

TCA  TTC  GAT  CTT  CCG  ACT  TAT  GAT  ATC  GAA  ATT  ACA  CCA  TTT  TTA           272
Ser  Phe  Asp  Leu  Pro  Thr  Tyr  Asp  Ile  Glu  Ile  Thr  Pro  Phe  Leu
                    80                        85                       90

GGG  AAG  ATA  TTA  GAT  GGG  AAG  AGC  CAC  AAG  TTC  GGG  TTT  AAT  GTT           317
Gly  Lys  Ile  Leu  Asp  Gly  Lys  Ser  His  Lys  Phe  Gly  Phe  Asn  Val
                    95                       100                      105

ACA  AAT  GCC  TTA  AAT  GTT  TGG  TAC  GTT  GAT  GCA  AAT  TTG  CAT  CTT           362
Thr  Asn  Ala  Leu  Asn  Val  Trp  Tyr  Val  Asp  Ala  Asn  Leu  His  Leu
                   110                       115                      120

TGG  TTG  GAC  AAA  CAG  AGC  ACA  AAA  ACT  GAA  GGA  AAG  CTT  TCG  AAA           407
Trp  Leu  Asp  Lys  Gln  Ser  Thr  Lys  Thr  Glu  Gly  Lys  Leu  Ser  Lys
                   125                       130                      135

CAT  AGT  AGC  TTG  CCC  CTT  GTT  GTT  TCC  CTG  GTT  TCA  GAT  TTC  AAG           452
His  Ser  Ser  Leu  Pro  Leu  Val  Val  Ser  Leu  Val  Ser  Asp  Phe  Lys
                   140                       145                      150

GGT  TTA  AAT  GGG  ACA  TTT  TTG  ACA  AGG  ACA  AGC  AGG  TCC  GTG  TCA           497
Gly  Leu  Asn  Gly  Thr  Phe  Leu  Thr  Arg  Thr  Ser  Arg  Ser  Val  Ser
                   155                       160                      165

TCC  ACT  GGA  TGG  GTG  AAG  TCT  TCC  TAT  GGG  AAT  ATC  ACA  ACC  CGT           542
Ser  Thr  Gly  Trp  Val  Lys  Ser  Ser  Tyr  Gly  Asn  Ile  Thr  Thr  Arg
                   170                       175                      180

TCA  ATT  CAA  GAC  TTC  TAT  TAC  AGT  AAT  TCA  ATG  GTC  CTG  GGG  AAA           587
Ser  Ile  Gln  Asp  Phe  Tyr  Tyr  Ser  Asn  Ser  Met  Val  Leu  Gly  Lys
                   185                       190                      195

GAT  GGT  AAT  ATG  CAG  ATA  GTC  AAC  CAG  AAG  ATC  ATT  TTC  AAT  GAC           632
Asp  Gly  Asn  Met  Gln  Ile  Val  Asn  Gln  Lys  Ile  Ile  Phe  Asn  Asp
                   200                       205                      210

TCA  GTT  TAT  ATT  AAC  CTG  CCA  TCC  TCC  TAT  GTT  CAC  TCA  CTG  ACA           677
```

```
Ser  Val  Tyr  Ile  Asn  Leu  Pro  Ser  Ser  Tyr  Val  His  Ser  Leu  Thr
               215                 220                           225

TCA  CAC  AAA  ACA  TTT  CCA  CTT  TAT  TTG  TAC  ACT  GAC  TTC  TTA  GGA    722
Ser  His  Lys  Thr  Phe  Pro  Leu  Tyr  Leu  Tyr  Thr  Asp  Phe  Leu  Gly
               230                 235                           240

CAA  GGA  AAT  GGA  ACT  TAT  TTA  TTG  ATT  ACA  AAT  GTG  GAC  TTG  GGA    767
Gln  Gly  Asn  Gly  Thr  Tyr  Leu  Leu  Ile  Thr  Asn  Val  Asp  Leu  Gly
               245                 250                           255

TTT  ATT  GAG  AAG  AAG  TCT  GGT  TTG  GGT  TTC  TCG  AAC  AGC  TCT  CTC    812
Phe  Ile  Glu  Lys  Lys  Ser  Gly  Leu  Gly  Phe  Ser  Asn  Ser  Ser  Leu
               260                 265                           270

AGA  AAT  CTG  CAG  AGT  GCT  GAG  GGC  AAT  ATG  GTT  GTG  AAA  AAC  AAT    857
Arg  Asn  Leu  Gln  Ser  Ala  Glu  Gly  Asn  Met  Val  Val  Lys  Asn  Asn
               275                 280                           285

TTG  GTT  GTG  AGT  GGA  TTG  GGG  AGC  ACT  CAG  CAA  GTC  TAT  AGA  TAT    902
Leu  Val  Val  Ser  Gly  Leu  Gly  Ser  Thr  Gln  Gln  Val  Tyr  Arg  Tyr
               290                 295                           300

GAT  GGT  GGT  AAA  TTC  TGT  TAC  TTC  AGA  AAT  ATA  AGC  AGC  TCA  AAC    947
Asp  Gly  Gly  Lys  Phe  Cys  Tyr  Phe  Arg  Asn  Ile  Ser  Ser  Ser  Asn
               305                 310                           315

TAC  ACA  ATA  CTC  TAT  GAC  AAG  GTG  GGG  AGC  AAA  TGC  AAC  AAA  AAA    992
Tyr  Thr  Ile  Leu  Tyr  Asp  Lys  Val  Gly  Ser  Lys  Cys  Asn  Lys  Lys
               320                 325                           330

TCG  TTG  TCT  AAT  TTG  GAT  TTT  GTC  TTA  AGC  AGA  CTG  TGG  CCT  TTT   1037
Ser  Leu  Ser  Asn  Leu  Asp  Phe  Val  Leu  Ser  Arg  Leu  Trp  Pro  Phe
               335                 340                           345

GGT  GCT  CGA  ATG  AAT  TTT  GCT  GGT  CTC  CGA  TTT  ACA  TGAGAACAAT      1083
Gly  Ala  Arg  Met  Asn  Phe  Ala  Gly  Leu  Arg  Phe  Thr
               350                 355

GAGGAAAGTC  TAGCTCATCC  ACATTCATGT  ATCTTCCTGT  TTGTTGGTAC  CTCAAATAAA   1143

TGTGTATTCT  GTACTCAATT  TCATTTTGTG  GGGATTCTTC  TAGATTGTAG  TTGAGGTATC   1203

TGCACTGCAC  CCAAGTGATT  CTGGTTTTAC  TTGGATTTGG  AATGATTACT  AAGAAGTGGA   1263

TCAGGTCAGC  TTGTCAGTAT  AATCAAAGTT  TATGCAGGAA  ATTTAAACC   ATTATTTTT    1323

GGCTTCGCA   TTTTTTGGCT  TTTAAATTTT  TAATATGATC  AATGCATTAA  AAATCCAAAG   1383

GGTTACCTAA  AAAAAAAAAA  AAAAAAGTCG  TGACTGGGAA  AACGACCTGC  AG           1435
```

( 2 ) INFORMATION FOR SEQ ID NO: 27:

( i ) SEQUENCE CHARACTERISTICS:
        ( A ) LENGTH: 1318
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 27:

```
TG  TTG  GAG  GTG  TAT  GTT  TCA  TTT  CAC  GAG  AAT  GAT  GAA  TTT  TGG  TAT      47
    Leu  Glu  Val  Tyr  Val  Ser  Phe  His  Glu  Asn  Asp  Glu  Phe  Trp  Tyr
     1              5                   10                       15

TCA  AAT  CTT  CCT  AAT  GAG  TAC  ATA  GCT  GCA  AAC  AAC  CTT  AGC  GGT         92
Ser  Asn  Leu  Pro  Asn  Glu  Tyr  Ile  Ala  Ala  Asn  Asn  Leu  Ser  Gly
               20                  25                           30

ACA  CCC  GGA  AAT  GGG  CCT  TTT  AGG  GAG  GTT  GTG  GTC  AGT  CTA  GAT        137
Thr  Pro  Gly  Asn  Gly  Pro  Phe  Arg  Glu  Val  Val  Val  Ser  Leu  Asp
               35                  40                           45

GGT  GAG  GTT  GTT  GGT  GCA  GTC  TGG  CCT  TTT  ACT  GTG  ATT  TTC  ACT        182
Gly  Glu  Val  Val  Gly  Ala  Val  Trp  Pro  Phe  Thr  Val  Ile  Phe  Thr
               50                  55                           60
```

```
GGA GGG ATC AAT CCT CTT TTA TGG AGA CCA ATT ACT GCA ATT GGC      227
Gly Gly Ile Asn Pro Leu Leu Trp Arg Pro Ile Thr Ala Ile Gly
            65              70              75

TCA TTC GAT CTT CCG ACT TAT GAT ATC GAA ATT ACA CCA TTT TTA      272
Ser Phe Asp Leu Pro Thr Tyr Asp Ile Glu Ile Thr Pro Phe Leu
            80              85              90

GGG AAG ATA TTA GAT GGG AAG AGC CAC AAG TTC GGG TTT AAT GTT      317
Gly Lys Ile Leu Asp Gly Lys Ser His Lys Phe Gly Phe Asn Val
            95             100             105

ACA AAT GCC TTA AAT GTT TGG TAC GTT GAT GCA AAT TTG CAT CTT      362
Thr Asn Ala Leu Asn Val Trp Tyr Val Asp Ala Asn Leu His Leu
           110             115             120

TGG TTG GAC AAA CAG AGC ACA AAA ACT GAA GGA AAG CTT TCG AAA      407
Trp Leu Asp Lys Gln Ser Thr Lys Thr Glu Gly Lys Leu Ser Lys
           125             130             135

CAT AGT AGC TTG CCC CTT GTT GTT TCC CTG GTT TCA GAT TTC AAG      452
His Ser Ser Leu Pro Leu Val Val Ser Leu Val Ser Asp Phe Lys
           140             145             150

GGT TTA AAT GGC ACA TTT TTG ACA AGG ACA AGC AGG TCC GTG TCA      497
Gly Leu Asn Gly Thr Phe Leu Thr Arg Thr Ser Arg Ser Val Ser
           155             160             165

TCA ACT GGA TGG GTG AAG TCT TCC TAT GGG AAT ATC ACA ACC CGT      542
Ser Thr Gly Trp Val Lys Ser Ser Tyr Gly Asn Ile Thr Thr Arg
           170             175             180

TCA ATT CAA GAC TTC TAT TAC AGT AAT TCA ATG GTC CTG GGG AAA      587
Ser Ile Gln Asp Phe Tyr Tyr Ser Asn Ser Met Val Leu Gly Lys
           185             190             195

GAT GGT AAT ATG CAG ATA GTC AAC CAG AAG ATC ATT TTC AAT GAC      632
Asp Gly Asn Met Gln Ile Val Asn Gln Lys Ile Ile Phe Asn Asp
           200             205             210

TCA GTT TAT ATT AAC CTG CCA TCC TCC TAT GTT CAC TCA CTG ACA      677
Ser Val Tyr Ile Asn Leu Pro Ser Ser Tyr Val His Ser Leu Thr
           215             220             225

TCA CAC AAA ACA TTT CCA CTT TAT TTG TAC ACT GAC TTC TTA GGA      722
Ser His Lys Thr Phe Pro Leu Tyr Leu Tyr Thr Asp Phe Leu Gly
           230             235             240

CAA GGA AAT GGA ACT TAT TTA TTG ATT ACA AAT GTG GAC TTG GGA      767
Gln Gly Asn Gly Thr Tyr Leu Leu Ile Thr Asn Val Asp Leu Gly
           245             250             255

TTT ATT GAG AAG AAG TCT GGT TTG GGA TTC TCG AAC AGC TCT CTC      812
Phe Ile Glu Lys Lys Ser Gly Leu Gly Phe Ser Asn Ser Ser Leu
           260             265             270

AGA AAT CTG CGG AGT GCT GAG GGC AAT ATG GTT GTG AAA AAC AAT      857
Arg Asn Leu Arg Ser Ala Glu Gly Asn Met Val Val Lys Asn Asn
           275             280             285

TTG GTT GTG AGT GGA TTG GGG AGC ACT CAG CAA ATC TAT AGA TAT      902
Leu Val Val Ser Gly Leu Gly Ser Thr Gln Gln Ile Tyr Arg Tyr
           290             295             300

GAT GGT GGT AAA TTC TGT TAC TTC AGA AAT ATA AGC AGC TCA AAC      947
Asp Gly Gly Lys Phe Cys Tyr Phe Arg Asn Ile Ser Ser Ser Asn
           305             310             315

TAC ACA ATA CTC TAT GAC AAG GTG GGG AGC AAA TGC AAC AAA AAA      992
Tyr Thr Ile Leu Tyr Asp Lys Val Gly Ser Lys Cys Asn Lys Lys
           320             325             330

TCG TTG TCT AAT TTG GAT TTT GTC TTA AGC AGA CTG TGG CCT TTT     1037
Ser Leu Ser Asn Leu Asp Phe Val Leu Ser Arg Leu Trp Pro Phe
           335             340             345

GGT GCT CGA ATG AAT TTT GCT GGT CTC CGA TTT ACA TGAGAACAAT      1083
Gly Ala Arg Met Asn Phe Ala Gly Leu Arg Phe Thr
           350             355
```

```
GAGGAAAGTC TAGCTCATCC ACATTCATGT ATCTTCCTGT TTGTTGGTAC CTCAAATAAA    1143

TGTGTATTCT GTACTCAATT TCATTTGTG  GGGATTCTTC TATATTGTAG TTGAGGTATC    1203

TGCACTGCAC CCAAGTGATT CTGGTTTTAC TTGGATTTGG AATGATTACT AAAAAGTGGA    1263

TCAGGTCAGC TTGTGCTAAA AAAAAAAAAA AAAAAAAGT  CGTGACTGGG AAAAC         1318
```

( 2 ) INFORMATION FOR SEQ ID NO: 28:

( i ) SEQUENCE CHARACTERISTICS:
        ( A ) LENGTH: 1426
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 28:

```
TTG  TTG  GAG  GTG  TAT  GTT  TCA  TTT  CAC  GAG  AAT  GAT  GAA  TTT  TGG  TAT    47
Leu  Leu  Glu  Val  Tyr  Val  Ser  Phe  His  Glu  Asn  Asp  Glu  Phe  Trp  Tyr
  1              5                        10                       15

TCA  AAT  CTT  CCT  AAT  GAG  TAC  ATA  GCT  GCA  AAC  AAC  CTT  AGC  GGT          92
Ser  Asn  Leu  Pro  Asn  Glu  Tyr  Ile  Ala  Ala  Asn  Asn  Leu  Ser  Gly
               20                       25                       30

ACA  CCT  GGA  AAT  GGG  CCT  TTT  AGG  GAG  GTT  GTG  GTC  AGT  CTA  GAT         137
Thr  Pro  Gly  Asn  Gly  Pro  Phe  Arg  Glu  Val  Val  Val  Ser  Leu  Asp
                    35                       40                       45

GGT  GAG  GTT  GTT  GGT  GCA  GTC  TGG  CCT  TTT  ACT  GTG  ATT  TTC  ACT         182
Gly  Glu  Val  Val  Gly  Ala  Val  Trp  Pro  Phe  Thr  Val  Ile  Phe  Thr
          50                       55                       60

GGA  GGG  ATC  AAT  CCT  CTT  TTA  TGG  AGA  CCA  ATT  ACT  GCA  ATT  GGC         227
Gly  Gly  Ile  Asn  Pro  Leu  Leu  Trp  Arg  Pro  Ile  Thr  Ala  Ile  Gly
                         65                       70                       75

TCA  TTC  GAT  CTT  CCG  ACT  TAT  GAT  ATC  GAA  ATT  ACA  CCA  TTT  TTA         272
Ser  Phe  Asp  Leu  Pro  Thr  Tyr  Asp  Ile  Glu  Ile  Thr  Pro  Phe  Leu
                    80                       85                       90

GGG  AAG  ATA  TTA  GAT  GGG  AAG  AGC  CAC  AAG  TTC  GGG  TTT  AAT  GTT         317
Gly  Lys  Ile  Leu  Asp  Gly  Lys  Ser  His  Lys  Phe  Gly  Phe  Asn  Val
               95                      100                      105

ACA  AAT  GCC  TTA  AAT  GTT  TGG  TAC  GTT  GAT  GCA  AAT  TTG  CAT  CTT         362
Thr  Asn  Ala  Leu  Asn  Val  Trp  Tyr  Val  Asp  Ala  Asn  Leu  His  Leu
                    110                      115                      120

TGG  TTG  GAC  AAA  CAG  AGC  ACA  AAA  ACT  GAA  GGA  AAG  CTT  TCG  AAA         407
Trp  Leu  Asp  Lys  Gln  Ser  Thr  Lys  Thr  Glu  Gly  Lys  Leu  Ser  Lys
          125                      130                      135

CAT  AGT  AGC  TTG  CCC  CTT  GTT  GTT  TCC  CTG  GTT  TCA  GAT  TTC  AAG         452
His  Ser  Ser  Leu  Pro  Leu  Val  Val  Ser  Leu  Val  Ser  Asp  Phe  Lys
                    140                      145                      150

GGT  TTA  AAT  GGG  ACA  TTT  TTG  ACA  AGG  ACA  AGC  AGG  TCC  GTG  TCA         497
Gly  Leu  Asn  Gly  Thr  Phe  Leu  Thr  Arg  Thr  Ser  Arg  Ser  Val  Ser
                         155                      160                      165

TCC  ACT  GGA  TGG  GTG  AAG  TCT  TCC  TAT  GGG  AAT  ATC  ACA  ACC  CGT         542
Ser  Thr  Gly  Trp  Val  Lys  Ser  Ser  Tyr  Gly  Asn  Ile  Thr  Thr  Arg
                    170                      175                      180

TCA  ATT  CAA  GAC  TTC  TAT  TAC  AGT  AAT  TCA  ATG  GTC  CTG  GGG  AAA         587
Ser  Ile  Gln  Asp  Phe  Tyr  Tyr  Ser  Asn  Ser  Met  Val  Leu  Gly  Lys
                    185                      190                      195

GAT  GGT  AAT  ATG  CAG  ATA  GTC  AAC  CAG  AAG  ATC  ATT  TTC  AAT  GAC         632
Asp  Gly  Asn  Met  Gln  Ile  Val  Asn  Gln  Lys  Ile  Ile  Phe  Asn  Asp
                    200                      205                      210

TCA  GTT  TAT  ATT  AAC  CTG  CCA  TCC  TCC  TAT  GTT  CAC  TCA  CTG  ACA         677
Ser  Val  Tyr  Ile  Asn  Leu  Pro  Ser  Ser  Tyr  Val  His  Ser  Leu  Thr
                    215                      220                      225
```

-continued

```
TCA CAC AAA ACA TTT CCA CTT TAT TTG TAC ACT GAC TTC TTA GGA      722
Ser His Lys Thr Phe Pro Leu Tyr Leu Tyr Thr Asp Phe Leu Gly
            230                 235                 240

CAA GGA AAT GGA ACT TAT TTA TTG ATT ACA AAT GTG GAC TTG GGA      767
Gln Gly Asn Gly Thr Tyr Leu Leu Ile Thr Asn Val Asp Leu Gly
            245                 250                 255

TTT ATT GAG AAG AAG TCT GGT TTG GGT TTC TCG AAC AGC TCT CTC      812
Phe Ile Glu Lys Lys Ser Gly Leu Gly Phe Ser Asn Ser Ser Leu
            260                 265                 270

AGA AAT CTG CAG AGT GCT GAG GGC AAT ATG GTT GTG AAA AAC AAT      857
Arg Asn Leu Gln Ser Ala Glu Gly Asn Met Val Val Lys Asn Asn
            275                 280                 285

TTG GTT GTG AGT GGA TTG GGG AGC ACT CAG CAA GTC TAT AGA TAT      902
Leu Val Val Ser Gly Leu Gly Ser Thr Gln Gln Val Tyr Arg Tyr
            290                 295                 300

GAT GGT GGT AAA TTC TGT TAC TTC AGA AAT ATA AGC AGC TCA AAC      947
Asp Gly Gly Lys Phe Cys Tyr Phe Arg Asn Ile Ser Ser Ser Asn
            305                 310                 315

TAC ACA ATA CTC TAT GAC AAG GTG GGG AGC AAA TGC AAC AAA AAA      992
Tyr Thr Ile Leu Tyr Asp Lys Val Gly Ser Lys Cys Asn Lys Lys
            320                 325                 330

TCG TTG TCT AAT TTG GAT TTT GTC TTA AGC AGA CTG TGG CCT TTT     1037
Ser Leu Ser Asn Leu Asp Phe Val Leu Ser Arg Leu Trp Pro Phe
            335                 340                 345

GGT GCT CGA ATG AAT TTT GCT GGT CTC CGA TTT ACA TGAGAACAAT      1083
Gly Ala Arg Met Asn Phe Ala Gly Leu Arg Phe Thr
            350                 355

GAGGAAAGTC TAGCTCATCC ACATTCATGT ATCTTCCTGT TTGTTGGTAC CTCAAATAAA  1143

TGTGTATTCT GTACTCAATT TCATTTGTG GGGATTCTTC TAGATTGTAG TTGAGGTATC  1203

TGCACTGCAC CCAAGTGATT CTGGTTTTAC TTGGATTTGG AATGATTACT AAGAAGTGGA  1263

TCAGGTCAGC TTGTCAGTAT AATCAAAGTT TATGCAGGAA ATTTTAAACC ATTATTTTTT  1323

GGCTTTCGCA TTTTTTGGCT TTTAAATTTT TAATATGATC AATGCATTAA AAATCCAAAG  1383

GGTTACCTAA AAAAAAAAAA AAAAAAGTCG TGACTGGGAA AAC                    1426
```

( 2 ) INFORMATION FOR SEQ ID NO: 29:

( i ) SEQUENCE CHARACTERISTICS:
        ( A ) LENGTH: 1358
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 29:

```
TG TTG GAG GTG TAT GTT TCA TTT CAC GAG AAT GAT GAA TTT TGG TAT    47
   Leu Glu Val Tyr Val Ser Phe His Glu Asn Asp Glu Phe Trp Tyr
   1               5                  10                  15

TCA AAT CTT CCT AAT GAG TAC ATA GCT GCA AAC AAC CTT AGC GGT       92
Ser Asn Leu Pro Asn Glu Tyr Ile Ala Ala Asn Asn Leu Ser Gly
             20                  25                  30

ACA CCC GGA AAT GGG CCT TTT AGG GAG GTT GTG GTC AGT CTA GAT      137
Thr Pro Gly Asn Gly Pro Phe Arg Glu Val Val Val Ser Leu Asp
             35                  40                  45

GGT GAG GTT GTT GGT GCA GTC TGG CCT TTT ACT GTG ATT TTC ACT      182
Gly Glu Val Val Gly Ala Val Trp Pro Phe Thr Val Ile Phe Thr
             50                  55                  60

GGA GGG ATC AAT CCT CTT TTA TGG AGA CCA ATT ACT GCA ATT GGC      227
Gly Gly Ile Asn Pro Leu Leu Trp Arg Pro Ile Thr Ala Ile Gly
             65                  70                  75
```

```
TCA TTC GAT CTT CCG ACT TAT GAT ATC GAA ATT ACA CCA TTT TTA       272
Ser Phe Asp Leu Pro Thr Tyr Asp Ile Glu Ile Thr Pro Phe Leu
        80                  85                  90

GGG AAG ATA TTA GAT GGG AAG AGC CAC AAG TTC GGG TTT AAT GTT       317
Gly Lys Ile Leu Asp Gly Lys Ser His Lys Phe Gly Phe Asn Val
        95                 100                 105

ACA AAT GCC TTA AAT GTT TGG TAC GTT GAT GCA AAT TTG CAT CTT       362
Thr Asn Ala Leu Asn Val Trp Tyr Val Asp Ala Asn Leu His Leu
       110                 115                 120

TGG TTG GAC AAA CAG AGC ACA AAA ACT GAA GGA AAG CTT TCG AAA       407
Trp Leu Asp Lys Gln Ser Thr Lys Thr Glu Gly Lys Leu Ser Lys
       125                 130                 135

CAT AGT AGC TTG CCC CTT GTT GTT TCC CTG GTT TCA GAT TTC AAG       452
His Ser Ser Leu Pro Leu Val Val Ser Leu Val Ser Asp Phe Lys
       140                 145                 150

GGT TTA AAT GGC ACA TTT TTG ACA AGG ACA AGC AGG TCC GTG TCA       497
Gly Leu Asn Gly Thr Phe Leu Thr Arg Thr Ser Arg Ser Val Ser
       155                 160                 165

TCA ACT GGA TGG GTG AAG TCT TCC TAT GGG AAT ATC ACA ACC CGT       542
Ser Thr Gly Trp Val Lys Ser Ser Tyr Gly Asn Ile Thr Thr Arg
       170                 175                 180

TCA ATT CAA GAC TTC TAT TAC AGT AAT TCA ATG GTC CTG GGG AAA       587
Ser Ile Gln Asp Phe Tyr Tyr Ser Asn Ser Met Val Leu Gly Lys
       185                 190                 195

GAT GGT AAT ATG CAG ATA GTC AAC CAG AAG ATC ATT TTC AAT GAC       632
Asp Gly Asn Met Gln Ile Val Asn Gln Lys Ile Ile Phe Asn Asp
       200                 205                 210

TCA GTT TAT ATT AAC CTG CCA TCC TCC TAT GTT CAC TCA CTG ACA       677
Ser Val Tyr Ile Asn Leu Pro Ser Ser Tyr Val His Ser Leu Thr
       215                 220                 225

TCA CAC AAA ACA TTT CCA CTT TAT TTG TAC ACT GAC TTC TTA GGA       722
Ser His Lys Thr Phe Pro Leu Tyr Leu Tyr Thr Asp Phe Leu Gly
       230                 235                 240

CAA GGA AAT GGA ACT TAT TTA TTG ATT ACA AAT GTG GAC TTG GGA       767
Gln Gly Asn Gly Thr Tyr Leu Leu Ile Thr Asn Val Asp Leu Gly
       245                 250                 255

TTT ATT GAG AAG AAG TCT GGT TTG GGA TTC TCG AAC AGC TCT CTC       812
Phe Ile Glu Lys Lys Ser Gly Leu Gly Phe Ser Asn Ser Ser Leu
       260                 265                 270

AGA AAT CTG CAG AGT GCT GAG GGC AAT ATG GTT GTG AAA AAC AAT       857
Arg Asn Leu Gln Ser Ala Glu Gly Asn Met Val Val Lys Asn Asn
       275                 280                 285

TTG GTT GTG AGT GGA TTG GAG AGC ACC CAG CAA GTC TAT AGA TAT       902
Leu Val Val Ser Gly Leu Glu Ser Thr Gln Gln Val Tyr Arg Tyr
       290                 295                 300

GAT GGT GGT AAA TTC TGT TAC TTC AGA AAT ATA AGC AGC TCA AAC       947
Asp Gly Gly Lys Phe Cys Tyr Phe Arg Asn Ile Ser Ser Ser Asn
       305                 310                 315

TAC ACA ATA CTC TAT GAC AAG GTG GGG AGC AAA TGC AAC AAA AAA       992
Tyr Thr Ile Leu Tyr Asp Lys Val Gly Ser Lys Cys Asn Lys Lys
       320                 325                 330

TCG TTG TCT AAT TTG GAT TTT GTC TTA AGC AGA CTG TGG CCT TTT      1037
Ser Leu Ser Asn Leu Asp Phe Val Leu Ser Arg Leu Trp Pro Phe
       335                 340                 345

GGT GCT CGA ATG AAT TTT GCT GGT CTC CGA TTT ACA TGAGAACAAT       1083
Gly Ala Arg Met Asn Phe Ala Gly Leu Arg Phe Thr
       350                 355

GAGGAAAGTC TAGCTCATCC ACATTCATGT ATCTTCCTGT TTGTTGGTAC CTCAAATAAA    1143

TGTGTATTCC GTACTCAATT TCATTTTGTG GGGATTCTTC TATATTGTAG TTGAGGTATC    1203
```

```
TGCACTGCAC   CCAAGTGATT   CTGGTTTTAC   TTGGATTTGG   AATGATTACT   AAAAAGTGGA   1263

TCAGGTCAGC   TTGTGCTATG   TTAGTATCAT   CAAAGTTTAT   GCAGGAAATT   TTAAACCATT   1323

AAAAAAAAAA   AAAAAAAAGT   CGTGACTGGG   AAAAC                                  1358
```

( 2 ) INFORMATION FOR SEQ ID NO: 30:

( i ) SEQUENCE CHARACTERISTICS:
        ( A ) LENGTH: 20
        ( B ) TYPE: amino acid
        ( D ) TOPOLOGY: linear ( i i ) MOLECULE TYPE: peptide ( x i ) SEQUENCE DESCRIPTION: SEQ ID NO: 30:

```
Glu  Pro  Thr  Pro  Leu  His  Asp  Thr  Pro  Pro  Thr  Val  Phe  Phe  Glu
 1              5                        10                       15

Val  Thr  Lys  Pro  Ile
               20
```

( 2 ) INFORMATION FOR SEQ ID NO: 31:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 31:

```
GARCCNACNC   CNCTNCAYGA   YAC                                                   23
```

( 2 ) INFORMATION FOR SEQ ID NO: 32:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 32:

```
GARCCNACNC   CNTTNCAYGA   YAC                                                   23
```

( 2 ) INFORMATION FOR SEQ ID NO: 33:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 33:

```
CAYGAYACNC   CNCCNACNGT                                                         20
```

( 2 ) INFORMATION FOR SEQ ID NO: 34:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 34:

GTNTT YTT YG ARGTNACNAA    20

( 2 ) INFORMATION FOR SEQ ID NO: 35:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) MOLECULE TYPE: other nucleic acid (DNA)

( x i ) SEQUENCE DESCRIPTION: SEQ ID NO: 35:

AACAACCTCA CCATCTAGAC TGACC    25

( 2 ) INFORMATION FOR SEQ ID NO: 36:

( i ) SEQUENCE CHARACTERISTICS:
    ( A ) LENGTH: 774
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO: 36:

| CAT | GAT | ACC | CCG | CCA | ACT | GTA | TTT | TTT | GAA | GTC | ACC | AAA | CCC | ATT | 45 |
| His | Asp | Thr | Pro | Pro | Thr | Val | Phe | Phe | Glu | Val | Thr | Lys | Pro | Ile | |
| 1 | | | | 5 | | | | | 10 | | | | | 15 | |

| GAA | GTA | CCA | AAA | ACC | AAG | CCG | TGT | TCC | CAG | CTC | ATT | CTC | CAG | CAT | 90 |
| Glu | Val | Pro | Lys | Thr | Lys | Pro | Cys | Ser | Gln | Leu | Ile | Leu | Gln | His | |
| | | | | 20 | | | | | 25 | | | | | 30 | |

| GAC | TTT | GCC | TAC | ACA | TAT | GGC | CAA | GCT | CCA | GTC | TTT | GCA | AAC | TAC | 135 |
| Asp | Phe | Ala | Tyr | Thr | Tyr | Gly | Gln | Ala | Pro | Val | Phe | Ala | Asn | Tyr | |
| | | | | 35 | | | | | 40 | | | | | 45 | |

| ACC | CCT | CCT | TCC | GAT | TGC | CCA | TCT | CAA | ACT | TTC | TCC | ACA | ATT | GTC | 180 |
| Thr | Pro | Pro | Ser | Asp | Cys | Pro | Ser | Gln | Thr | Phe | Ser | Thr | Ile | Val | |
| | | | | 50 | | | | | 55 | | | | | 60 | |

| CTT | GAA | TGG | AAA | GCT | ACC | TGC | AGA | GGA | AGG | CAA | TTT | GAC | CGC | ATT | 225 |
| Leu | Glu | Trp | Lys | Ala | Thr | Cys | Arg | Gly | Arg | Gln | Phe | Asp | Arg | Ile | |
| | | | | 65 | | | | | 70 | | | | | 75 | |

| TTC | GGG | GTT | TGG | CTT | GGT | GGG | GTT | GAG | ATT | CTC | AGG | AGC | TGC | ACA | 270 |
| Phe | Gly | Val | Trp | Leu | Gly | Gly | Val | Glu | Ile | Leu | Arg | Ser | Cys | Thr | |
| | | | | 80 | | | | | 85 | | | | | 90 | |

| GCA | GAA | CCA | AGG | CCT | AAT | GGG | ATT | GTT | TGG | ACT | GTC | GAG | AAG | GAC | 315 |
| Ala | Glu | Pro | Arg | Pro | Asn | Gly | Ile | Val | Trp | Thr | Val | Glu | Lys | Asp | |
| | | | | 95 | | | | | 100 | | | | | 105 | |

| ATC | ACA | AGG | TAC | TAT | TCA | CTG | CTT | AAG | AGT | AAT | CAA | ACA | CTT | GCT | 360 |
| Ile | Thr | Arg | Tyr | Tyr | Ser | Leu | Leu | Lys | Ser | Asn | Gln | Thr | Leu | Ala | |
| | | | | 110 | | | | | 115 | | | | | 120 | |

| GTT | TAT | CTT | GGC | AAT | TTG | ATA | GAT | AAA | ACC | TAC | ACT | GGG | ATT | TAT | 405 |
| Val | Tyr | Leu | Gly | Asn | Leu | Ile | Asp | Lys | Thr | Tyr | Thr | Gly | Ile | Tyr | |
| | | | | 125 | | | | | 130 | | | | | 135 | |

| CAT | GTG | AAT | ATA | AGC | CTT | CAT | TTT | TAC | CCT | GCT | AAA | GAG | AAA | TTG | 450 |
| His | Val | Asn | Ile | Ser | Leu | His | Phe | Tyr | Pro | Ala | Lys | Glu | Lys | Leu | |
| | | | | 140 | | | | | 145 | | | | | 150 | |

| AAT | TCT | TTT | CAG | CAA | AAG | TTG | GAT | AAT | TTG | GCA | TCT | GGG | TAC | CAT | 495 |
| Asn | Ser | Phe | Gln | Gln | Lys | Leu | Asp | Asn | Leu | Ala | Ser | Gly | Tyr | His | |
| | | | | 155 | | | | | 160 | | | | | 165 | |

| TCT | TGG | GCT | GAT | TTG | ATT | TTA | CCC | GTT | TCG | AGA | AAT | CTG | CCT | TTG | 540 |
| Ser | Trp | Ala | Asp | Leu | Ile | Leu | Pro | Val | Ser | Arg | Asn | Leu | Pro | Leu | |
| | | | | 170 | | | | | 175 | | | | | 180 | |

| | | | | | | | | | | | | | | |
|---|---|---|---|---|---|---|---|---|---|---|---|---|---|---|
| AAT | GAT | GGG | TTG | TGG | TTT | GAA | GTT | CAG | AAT | TCA | AAT | GAT | ACG | GAA | 585 |
| Asn | Asp | Gly | Leu | Trp | Phe | Glu | Val | Gln | Asn | Ser | Asn | Asp | Thr | Glu | |
| | | | 185 | | | | | 190 | | | | | 195 | | |
| TTG | AAG | GAG | TTC | AAG | ATT | CCA | CAA | AAT | GCT | TAT | AGG | GCT | GTG | TTG | 630 |
| Leu | Lys | Glu | Phe | Lys | Ile | Pro | Gln | Asn | Ala | Tyr | Arg | Ala | Val | Leu | |
| | | | | 200 | | | | | 205 | | | | | 210 | |
| GAG | GTG | TAT | GTT | TCA | TTT | CAC | GAG | AAT | GAT | GAA | TTT | TGG | TAT | TCA | 675 |
| Glu | Val | Tyr | Val | Ser | Phe | His | Glu | Asn | Asp | Glu | Phe | Trp | Tyr | Ser | |
| | | | | 215 | | | | | 220 | | | | | 225 | |
| AAT | CTT | CCT | AAT | GAG | TAC | ATA | GCT | GCA | AAC | AAC | CTT | AGC | GGT | ACA | 720 |
| Asn | Leu | Pro | Asn | Glu | Tyr | Ile | Ala | Ala | Asn | Asn | Leu | Ser | Gly | Thr | |
| | | | | 230 | | | | | 235 | | | | | 240 | |
| CCC | GGA | AAT | GGG | CCT | TTT | AGG | GAG | GTT | GTG | GTC | AGT | CTA | GAT | GGT | 765 |
| Pro | Gly | Asn | Gly | Pro | Phe | Arg | Glu | Val | Val | Val | Ser | Leu | Asp | Gly | |
| | | | | 245 | | | | | 250 | | | | | 255 | |
| GAG | GTT | GTT | | | | | | | | | | | | | 774 |
| Glu | Val | Val | | | | | | | | | | | | | |

( 2 ) INFORMATION FOR SEQ ID NO: 37:

( i ) SEQUENCE CHARACTERISTICS:
    ( A ) LENGTH: 774
    ( B ) TYPE: nucleic acid
    ( C ) STRANDEDNESS: double
    ( D ) TOPOLOGY: linear ( i i ) MOLECULE TYPE: cDNA to mRNA ( x i ) SEQUENCE DESCRIPTION: SEQ ID NO: 37:

| | | | | | | | | | | | | | | |
|---|---|---|---|---|---|---|---|---|---|---|---|---|---|---|
| CAT | GAC | ACG | CCG | CCG | ACC | GTA | TTT | TTT | GAA | GTC | ACC | AAA | CCC | ATT | 45 |
| His | Asp | Thr | Pro | Pro | Thr | Val | Phe | Phe | Glu | Val | Thr | Lys | Pro | Ile | |
| 1 | | | | 5 | | | | | 10 | | | | | 15 | |
| GAA | GTA | CCA | AAA | ACC | AAG | CCG | TGT | TCC | CAG | CTC | ATT | CTC | CAG | CAT | 90 |
| Glu | Val | Pro | Lys | Thr | Lys | Pro | Cys | Ser | Gln | Leu | Ile | Leu | Gln | His | |
| | | | | 20 | | | | | 25 | | | | | 30 | |
| GAC | TTT | GCC | TAC | ACA | TAT | GGC | CAA | GCT | CCA | GTC | TTT | GCA | AAC | TAC | 135 |
| Asp | Phe | Ala | Tyr | Thr | Tyr | Gly | Gln | Ala | Pro | Val | Phe | Ala | Asn | Tyr | |
| | | | | 35 | | | | | 40 | | | | | 45 | |
| ACC | CCT | CCT | TCC | GAT | TGC | CCA | TCT | CAA | ACT | TTC | TCC | ACA | ATT | GTC | 180 |
| Thr | Pro | Pro | Ser | Asp | Cys | Pro | Ser | Gln | Thr | Phe | Ser | Thr | Ile | Val | |
| | | | | 50 | | | | | 55 | | | | | 60 | |
| CTT | GAA | TGG | AAA | GCT | ACC | TGC | AGA | GGA | AGG | CAA | TTT | GAC | CGC | ATT | 225 |
| Leu | Glu | Trp | Lys | Ala | Thr | Cys | Arg | Gly | Arg | Gln | Phe | Asp | Arg | Ile | |
| | | | | 65 | | | | | 70 | | | | | 75 | |
| TTC | GGG | GTT | TGG | CTT | GGT | GGG | GTT | GAG | ATT | CTC | AGG | AGC | TGC | ACA | 270 |
| Phe | Gly | Val | Trp | Leu | Gly | Gly | Val | Glu | Ile | Leu | Arg | Ser | Cys | Thr | |
| | | | | 80 | | | | | 85 | | | | | 90 | |
| GCA | GAA | CCA | AGG | CCT | AAT | GGG | ATT | GTT | TGG | ACT | GTC | GAG | AAG | GAC | 315 |
| Ala | Glu | Pro | Arg | Pro | Asn | Gly | Ile | Val | Trp | Thr | Val | Glu | Lys | Asp | |
| | | | | 95 | | | | | 100 | | | | | 105 | |
| ATC | ACA | AGG | TAC | TAT | TCA | CTG | CTT | AAG | AGT | AAT | CAA | ACA | CTT | GCT | 360 |
| Ile | Thr | Arg | Tyr | Tyr | Ser | Leu | Leu | Lys | Ser | Asn | Gln | Thr | Leu | Ala | |
| | | | | 110 | | | | | 115 | | | | | 120 | |
| GTT | TAT | CTT | GGC | AAT | TTG | ATA | GAT | AAA | ACC | TAC | ACT | GGG | ATT | TAT | 405 |
| Val | Tyr | Leu | Gly | Asn | Leu | Ile | Asp | Lys | Thr | Tyr | Thr | Gly | Ile | Tyr | |
| | | | | 125 | | | | | 130 | | | | | 135 | |
| CAT | GTG | AAT | ATA | AGC | CTT | CAT | TTT | TAC | CCT | GCT | AAA | GAG | AAA | TTG | 450 |
| His | Val | Asn | Ile | Ser | Leu | His | Phe | Tyr | Pro | Ala | Lys | Glu | Lys | Leu | |
| | | | | 140 | | | | | 145 | | | | | 150 | |
| AAT | TCT | TTT | CAG | CAA | AAG | TTG | GAT | AAT | TTG | GCA | TCT | GGG | TAC | CAT | 495 |
| Asn | Ser | Phe | Gln | Gln | Lys | Leu | Asp | Asn | Leu | Ala | Ser | Gly | Tyr | His | |
| | | | | 155 | | | | | 160 | | | | | 165 | |

```
TCT TGG GCT GAT TTG ATT TTA CCC GTT TCG AGA AAT CTG CCT TTG    540
Ser Trp Ala Asp Leu Ile Leu Pro Val Ser Arg Asn Leu Pro Leu
            170             175             180

AAT GAC GGG TTG TGG TTT GAA GTT CAG AAT TCA AAT GAT ACG GAA    585
Asn Asp Gly Leu Trp Phe Glu Val Gln Asn Ser Asn Asp Thr Glu
            185             190             195

TTG AAG GAG TTC AAG ATT CCA CAA AAT GCT TAT AGG GCT GTG TTG    630
Leu Lys Glu Phe Lys Ile Pro Gln Asn Ala Tyr Arg Ala Val Leu
            200             205             210

GAG GTG TAT GTT TCA TTT CAC GAG AAT GAT GAA TTT TGG TAT TCA    675
Glu Val Tyr Val Ser Phe His Glu Asn Asp Glu Phe Trp Tyr Ser
            215             220             225

AAT CTT CCT AAT GAG TAC ATA GCT GCA AAC AAC CTT AGC GGT ACA    720
Asn Leu Pro Asn Glu Tyr Ile Ala Ala Asn Asn Leu Ser Gly Thr
            230             235             240

CCC GGA AAT GGG CCT TTT AGG GAG GTT GTG GTC AGT CTA GAT GGT    765
Pro Gly Asn Gly Pro Phe Arg Glu Val Val Val Ser Leu Asp Gly
            245             250             255

GAG GTT GTT                                                     774
Glu Val Val
```

( 2 ) INFORMATION FOR SEQ ID NO: 38:

( i ) SEQUENCE CHARACTERISTICS:
      ( A ) LENGTH: 774
      ( B ) TYPE: nucleic acid
      ( C ) STRANDEDNESS: double
      ( D ) TOPOLOGY: linear ( i i ) MOLECULE TYPE: cDNA to mRNA ( x i ) SEQUENCE DESCRIPTION: SEQ ID NO: 38:

```
CAC GAT ACA CCG CCG ACA GTA TTT TTT GAA GTC ACC AAA CCC ATT     45
His Asp Thr Pro Pro Thr Val Phe Phe Glu Val Thr Lys Pro Ile
 1               5              10              15

GAA GTA CCA AAA ACC AAG CCG TGT TCC CAG CTC ATT CTC CAG CAT     90
Glu Val Pro Lys Thr Lys Pro Cys Ser Gln Leu Ile Leu Gln His
            20              25              30

GAC TTT GCC TAC ACA TAT GGC CAA GCT CCA GTC TTT GCA AAC TAC    135
Asp Phe Ala Tyr Thr Tyr Gly Gln Ala Pro Val Phe Ala Asn Tyr
            35              40              45

ACC CCT CCT TCC GAT TGC CCA TCT CAA ACT TTC TCC ACA ATT GTC    180
Thr Pro Pro Ser Asp Cys Pro Ser Gln Thr Phe Ser Thr Ile Val
            50              55              60

CTT GAA TGG AAA GCT ACC TGC AGA GGA AGG CAA TTT GAC CGC ATT    225
Leu Glu Trp Lys Ala Thr Cys Arg Gly Arg Gln Phe Asp Arg Ile
            65              70              75

TTC GGG GTT TGG CTT GGT GGG GTT GAG ATT CTC AGG AGC TGC ACA    270
Phe Gly Val Trp Leu Gly Gly Val Glu Ile Leu Arg Ser Cys Thr
            80              85              90

GCA GAA CCA AGG CCT AAT GGG ATT GTT TGG ACT GTC GAG AAG GAC    315
Ala Glu Pro Arg Pro Asn Gly Ile Val Trp Thr Val Glu Lys Asp
            95             100             105

ATC ACA AGG TAC TAT TCA CTG CTT AAG AGT AAT CAA ACA CTT GCT    360
Ile Thr Arg Tyr Tyr Ser Leu Leu Lys Ser Asn Gln Thr Leu Ala
           110             115             120

GTT TAT CTT GGC AAT TTG ATA GAT AAA ACC TAC ACT GGG ATT TAT    405
Val Tyr Leu Gly Asn Leu Ile Asp Lys Thr Tyr Thr Gly Ile Tyr
           125             130             135

CAT GTG AAT ATA AGC CTT CAT TTT TAC CCT GCT AAA GAG AAA TTG    450
His Val Asn Ile Ser Leu His Phe Tyr Pro Ala Lys Glu Lys Leu
           140             145             150
```

```
AAT  TCT  TTT  CAG  CAA  AAG  TTG  GAT  AAT  TTG  GCA  TCT  GGG  TAC  CAT      495
Asn  Ser  Phe  Gln  Gln  Lys  Leu  Asp  Asn  Leu  Ala  Ser  Gly  Tyr  His
               155                 160                           165

TCT  TGG  GCT  GAT  TTG  ATT  TTA  CCC  GTT  TCG  AGA  AAT  CTG  CCT  TTG      540
Ser  Trp  Ala  Asp  Leu  Ile  Leu  Pro  Val  Ser  Arg  Asn  Leu  Pro  Leu
               170                 175                           180

AAT  GAT  GGG  TTG  TGG  TTT  GAA  GTT  CAG  AAT  TCA  AAT  GAT  ACG  GAA      585
Asn  Asp  Gly  Leu  Trp  Phe  Glu  Val  Gln  Asn  Ser  Asn  Asp  Thr  Glu
               185                 190                           195

TTG  AAG  GAG  TTC  AAG  ATT  CCA  CAA  AAT  GCT  TAT  AGG  GCT  GTG  TTG      630
Leu  Lys  Glu  Phe  Lys  Ile  Pro  Gln  Asn  Ala  Tyr  Arg  Ala  Val  Leu
               200                 205                           210

GAG  GTG  TAT  GTT  TCA  TTT  CAC  GAG  AAT  GAT  GAA  TTT  TGG  TAT  TCA      675
Glu  Val  Tyr  Val  Ser  Phe  His  Glu  Asn  Asp  Glu  Phe  Trp  Tyr  Ser
               215                 220                           225

AAT  CTT  CCT  AAT  GAG  TAC  ATA  GCT  GCA  AAC  AAC  CTT  AGC  GGT  ACA      720
Asn  Leu  Pro  Asn  Glu  Tyr  Ile  Ala  Ala  Asn  Asn  Leu  Ser  Gly  Thr
               230                 235                           240

CCC  GGA  AAT  GGG  CCT  TTT  AGG  GAG  GTT  GTG  GTC  AGT  CTA  GAT  GGT      765
Pro  Gly  Asn  Gly  Pro  Phe  Arg  Glu  Val  Val  Val  Ser  Leu  Asp  Gly
               245                 250                           255

GAG  GTT  GTT                                                                   774
Glu  Val  Val
```

( 2 ) INFORMATION FOR SEQ ID NO: 39:

( i ) SEQUENCE CHARACTERISTICS:
        ( A ) LENGTH: 774
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 39:

```
CAC  GAC  ACG  CCG  CCG  ACC  GTA  TTT  TTT  GAA  GTC  ACC  AAA  CCC  ATT       45
His  Asp  Thr  Pro  Pro  Thr  Val  Phe  Phe  Glu  Val  Thr  Lys  Pro  Ile
 1                    5                  10                            15

GAA  GTA  CCA  AAA  ACC  AAG  TCG  TGT  TCC  CAG  CTC  ATT  CTC  CAG  CAT       90
Glu  Val  Pro  Lys  Thr  Lys  Ser  Cys  Ser  Gln  Leu  Ile  Leu  Gln  His
                20                  25                            30

GAC  TTT  GCC  TAC  ACA  TAT  GGC  CAA  GCT  CCA  GTC  TTT  GCA  AAC  TAC      135
Asp  Phe  Ala  Tyr  Thr  Tyr  Gly  Gln  Ala  Pro  Val  Phe  Ala  Asn  Tyr
                35                  40                            45

ACC  CCT  CCT  TCC  GAT  TGC  CCA  TCT  CAA  ACT  TTC  TCC  ACA  ATT  GTC      180
Thr  Pro  Pro  Ser  Asp  Cys  Pro  Ser  Gln  Thr  Phe  Ser  Thr  Ile  Val
                50                  55                            60

CTT  GAA  TGG  AAA  GCT  ACC  TGC  AGA  GGA  AGG  CAA  TTT  GAC  CGC  ATT      225
Leu  Glu  Trp  Lys  Ala  Thr  Cys  Arg  Gly  Arg  Gln  Phe  Asp  Arg  Ile
                65                  70                            75

TTC  GGG  GTT  TGG  CTT  GGT  GGG  GTT  GAG  ATT  CTC  AGG  AGC  TGC  ACA      270
Phe  Gly  Val  Trp  Leu  Gly  Gly  Val  Glu  Ile  Leu  Arg  Ser  Cys  Thr
                80                  85                            90

GCA  GAA  CCA  AGG  CCT  AAT  GGG  ATT  GTT  TGG  ACT  GTC  GAG  AAG  GAC      315
Ala  Glu  Pro  Arg  Pro  Asn  Gly  Ile  Val  Trp  Thr  Val  Glu  Lys  Asp
                95                 100                           105

ATC  ACA  AGG  TAC  TAT  TCA  CTG  CTT  AAG  AGT  AAT  CAA  ACA  CTT  GCT      360
Ile  Thr  Arg  Tyr  Tyr  Ser  Leu  Leu  Lys  Ser  Asn  Gln  Thr  Leu  Ala
               110                 115                           120

GTT  TAT  CTT  GGC  AAT  TTG  ATA  GAT  AAA  ACC  TAC  ACT  GGG  ATT  TAT      405
Val  Tyr  Leu  Gly  Asn  Leu  Ile  Asp  Lys  Thr  Tyr  Thr  Gly  Ile  Tyr
               125                 130                           135
```

| | | | | | | | | | | | | | | | |
|---|---|---|---|---|---|---|---|---|---|---|---|---|---|---|---|
| CAT | GTG | AAT | ATA | AGC | CTT | CAT | TTT | TAC | CCT | GCT | GAA | GAG | AAA | TTG | 450 |
| His | Val | Asn | Ile | Ser | Leu | His | Phe | Tyr | Pro | Ala | Glu | Glu | Lys | Leu | |
| | | | 140 | | | | | 145 | | | | | | 150 | |
| AAT | TCT | TTT | CAG | CAA | AAG | TTG | GAT | AAT | TTG | GCA | TCT | GGG | TAC | CAT | 495 |
| Asn | Ser | Phe | Gln | Gln | Lys | Leu | Asp | Asn | Leu | Ala | Ser | Gly | Tyr | His | |
| | | | | 155 | | | | | 160 | | | | | 165 | |
| TCT | TGG | GCT | GAT | TTG | ATT | TTA | CCC | ATT | TCG | AGA | AAT | CTG | CCT | TTG | 540 |
| Ser | Trp | Ala | Asp | Leu | Ile | Leu | Pro | Ile | Ser | Arg | Asn | Leu | Pro | Leu | |
| | | | | 170 | | | | | 175 | | | | | 180 | |
| AAT | GAT | GGG | TTG | TGG | TTT | GAA | GTT | CAG | AAT | TCA | AAT | GAT | ACG | GAA | 585 |
| Asn | Asp | Gly | Leu | Trp | Phe | Glu | Val | Gln | Asn | Ser | Asn | Asp | Thr | Glu | |
| | | | | 185 | | | | | 190 | | | | | 195 | |
| TTG | AAG | GAG | TTC | AAG | ATT | CCA | CAA | AAT | GCT | TAT | AGG | GCT | GTG | TTG | 630 |
| Leu | Lys | Glu | Phe | Lys | Ile | Pro | Gln | Asn | Ala | Tyr | Arg | Ala | Val | Leu | |
| | | | | 200 | | | | | 205 | | | | | 210 | |
| GAG | GTG | TAT | GTT | TCA | TTT | CAC | GAG | AAT | GAT | GAA | TTT | TGG | TAT | TCA | 675 |
| Glu | Val | Tyr | Val | Ser | Phe | His | Glu | Asn | Asp | Glu | Phe | Trp | Tyr | Ser | |
| | | | | 215 | | | | | 220 | | | | | 225 | |
| AAT | CTT | CCT | AAT | GAG | TAC | ATA | GCT | GCA | AAC | AAC | CTT | AGC | GGT | ACA | 720 |
| Asn | Leu | Pro | Asn | Glu | Tyr | Ile | Ala | Ala | Asn | Asn | Leu | Ser | Gly | Thr | |
| | | | | 230 | | | | | 235 | | | | | 240 | |
| CCT | GGA | AAT | GGG | CCT | TTT | AGG | GAG | GTT | GTG | GTC | AGT | CTA | GAT | GGT | 765 |
| Pro | Gly | Asn | Gly | Pro | Phe | Arg | Glu | Val | Val | Val | Ser | Leu | Asp | Gly | |
| | | | | 245 | | | | | 250 | | | | | 255 | |
| GAG | GTT | GTT | | | | | | | | | | | | | 774 |
| Glu | Val | Val | | | | | | | | | | | | | |

( 2 ) INFORMATION FOR SEQ ID NO: 40:

( i ) SEQUENCE CHARACTERISTICS:
        ( A ) LENGTH: 774
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 40:

| | | | | | | | | | | | | | | | |
|---|---|---|---|---|---|---|---|---|---|---|---|---|---|---|---|
| CAC | GAC | ACA | CCG | CCG | ACT | GTA | TTT | TTT | GAA | GTC | ACC | AAA | CCC | ATT | 45 |
| His | Asp | Thr | Pro | Pro | Thr | Val | Phe | Phe | Glu | Val | Thr | Lys | Pro | Ile | |
| 1 | | | | 5 | | | | | 10 | | | | | 15 | |
| GAA | GTA | CCA | AAA | ACC | AAG | CCG | TGT | TCC | CAG | CTC | ATT | CTC | CAG | CAT | 90 |
| Glu | Val | Pro | Lys | Thr | Lys | Pro | Cys | Ser | Gln | Leu | Ile | Leu | Gln | His | |
| | | | | 20 | | | | | 25 | | | | | 30 | |
| GAC | TTT | GCC | TAC | ACA | TAT | GGC | CAA | GCT | CCA | GTC | TTT | GCA | AAC | TAC | 135 |
| Asp | Phe | Ala | Tyr | Thr | Tyr | Gly | Gln | Ala | Pro | Val | Phe | Ala | Asn | Tyr | |
| | | | | 35 | | | | | 40 | | | | | 45 | |
| ACC | CCT | CCT | TCC | GAT | TGC | CCA | TCT | CAA | ACT | TTC | TCC | ACA | ATT | GTC | 180 |
| Thr | Pro | Pro | Ser | Asp | Cys | Pro | Ser | Gln | Thr | Phe | Ser | Thr | Ile | Val | |
| | | | | 50 | | | | | 55 | | | | | 60 | |
| CTT | GAA | TGG | AAA | GCT | ACC | TGC | AGA | AGA | AGG | CAA | TTT | GAC | CGC | ATT | 225 |
| Leu | Glu | Trp | Lys | Ala | Thr | Cys | Arg | Arg | Arg | Gln | Phe | Asp | Arg | Ile | |
| | | | | 65 | | | | | 70 | | | | | 75 | |
| TTC | GGG | GTT | TGG | CTT | GGT | GGG | GTT | GAG | ATT | CTC | AGG | AGC | TGC | ACA | 270 |
| Phe | Gly | Val | Trp | Leu | Gly | Gly | Val | Glu | Ile | Leu | Arg | Ser | Cys | Thr | |
| | | | | 80 | | | | | 85 | | | | | 90 | |
| GCA | GAA | CCA | AGG | CCT | AAT | GGG | ATT | GTT | TGG | ACT | GTC | GAG | AAG | GAC | 315 |
| Ala | Glu | Pro | Arg | Pro | Asn | Gly | Ile | Val | Trp | Thr | Val | Glu | Lys | Asp | |
| | | | | 95 | | | | | 100 | | | | | 105 | |
| ATC | ACA | AGG | TAC | TAT | TCA | CTG | CTT | AAG | AGT | AAT | CAA | ACA | CTT | GCT | 360 |
| Ile | Thr | Arg | Tyr | Tyr | Ser | Leu | Leu | Lys | Ser | Asn | Gln | Thr | Leu | Ala | |
| | | | | 110 | | | | | 115 | | | | | 120 | |

```
GTT TAT CTT GGC AAT TTG ATA GAT AAA ACC TAC ACT GGG ATT TAT    405
Val Tyr Leu Gly Asn Leu Ile Asp Lys Thr Tyr Thr Gly Ile Tyr
            125                 130                 135

CAT GTG AAT ATA AGC CTT CAT TTT TAC CCT GCT GAA GAG AAA TTG    450
His Val Asn Ile Ser Leu His Phe Tyr Pro Ala Glu Glu Lys Leu
            140                 145                 150

AAT TCT TTT CAG CAA AAG TTG GAT AAT TTG GCA TCT GGG TAC CAT    495
Asn Ser Phe Gln Gln Lys Leu Asp Asn Leu Ala Ser Gly Tyr His
            155                 160                 165

TCT TGG GCT GAT TTG ATT TTA CCC ATT TCG AGA AAT CTG CCT TTG    540
Ser Trp Ala Asp Leu Ile Leu Pro Ile Ser Arg Asn Leu Pro Leu
            170                 175                 180

AAT GAT GGG TTG TGG TTT GAA GTT CAG AAT TCA AAT GAT ACG GAA    585
Asn Asp Gly Leu Trp Phe Glu Val Gln Asn Ser Asn Asp Thr Glu
            185                 190                 195

TTG AAG GAG TTC AAG ATT CCA CAA AAT GCT TAT AGG GCT GTG TTG    630
Leu Lys Glu Phe Lys Ile Pro Gln Asn Ala Tyr Arg Ala Val Leu
            200                 205                 210

GAG GTG TAT GTT TCA TTT CAC GAG AAT GAT GAA TTT TGG TAT TCA    675
Glu Val Tyr Val Ser Phe His Glu Asn Asp Glu Phe Trp Tyr Ser
            215                 220                 225

AAT CTT CCT AAT GAG TAC ATA GCT GCA AAC AAC CTT AGC GGT ACA    720
Asn Leu Pro Asn Glu Tyr Ile Ala Ala Asn Asn Leu Ser Gly Thr
            230                 235                 240

CCT GGA AAT GGG CCT TTT AGG GAG GTT GTG GTC AGT CTA GAT GGT    765
Pro Gly Asn Gly Pro Phe Arg Glu Val Val Val Ser Leu Asp Gly
            245                 250                 255

GAG GTT GTT                                                    774
Glu Val Val
```

( 2 ) INFORMATION FOR SEQ ID NO: 41:

( i ) SEQUENCE CHARACTERISTICS:
        ( A ) LENGTH: 774
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 41:

```
CAC GAT ACA CCG CCG ACT GTA TTT TTT GAA GTC ACC AAA CCC ATT     45
His Asp Thr Pro Pro Thr Val Phe Phe Glu Val Thr Lys Pro Ile
1               5                   10                  15

GAA GTA CCA AAA ACC AAG CCG TGT TCC CAG CTC ATT CTC CAG CAT     90
Glu Val Pro Lys Thr Lys Pro Cys Ser Gln Leu Ile Leu Gln His
            20                  25                  30

GAC TTT GCC TAC ACA TAT GGC CAA GCT CCA GTC TTT GCA AAC TAC    135
Asp Phe Ala Tyr Thr Tyr Gly Gln Ala Pro Val Phe Ala Asn Tyr
            35                  40                  45

ACC CCT CCT TCC GAT TGC CCA TCT CAA ACT TTC TCC ACA ATT GTC    180
Thr Pro Pro Ser Asp Cys Pro Ser Gln Thr Phe Ser Thr Ile Val
            50                  55                  60

CTT GAA TGG AAA GCT ACC TGC AGA GGA AGG CAA TTT GAC CGC ATT    225
Leu Glu Trp Lys Ala Thr Cys Arg Gly Arg Gln Phe Asp Arg Ile
            65                  70                  75

TTC GGG GTT TGG CTT GGT GGG GTT GAG ATT CTC AGG AGC TGC ACA    270
Phe Gly Val Trp Leu Gly Gly Val Glu Ile Leu Arg Ser Cys Thr
            80                  85                  90

GCA GAA CCA AGG CCT AAT GGG ATT GTT TGG ACT GTC GAG AAG GAC    315
Ala Glu Pro Arg Pro Asn Gly Ile Val Trp Thr Val Glu Lys Asp
            95                  100                 105
```

```
ATC ACA AGG TAC TAT TCA CTG CTT AAG AGT AAT CAA ACA CTT GCT     360
Ile Thr Arg Tyr Tyr Ser Leu Leu Lys Ser Asn Gln Thr Leu Ala
            110             115                 120

GTT TAT CTT GGC AAT TTG ATA GAT AAA ACC TAC ACT GGG ATT TAT     405
Val Tyr Leu Gly Asn Leu Ile Asp Lys Thr Tyr Thr Gly Ile Tyr
            125             130                 135

CAT GTG AAT ATA AGC CTT CAT TTT TAC CCT GCT AAA GAG AAA TTG     450
His Val Asn Ile Ser Leu His Phe Tyr Pro Ala Lys Glu Lys Leu
            140             145                 150

AAT TCT TTT CAG CAA AAG TTG GAT AAT TTG GCA TCT GGG TAC CAT     495
Asn Ser Phe Gln Gln Lys Leu Asp Asn Leu Ala Ser Gly Tyr His
            155             160                 165

TCT TGG GCT GAT TTG ATT TTA CCC GTT TCG AGA AAT CTG CCT TTG     540
Ser Trp Ala Asp Leu Ile Leu Pro Val Ser Arg Asn Leu Pro Leu
            170             175                 180

AAT GAT GGG TTG TGG TTT GAA GTT CAG AAT TCA AAT GAT ACG GAA     585
Asn Asp Gly Leu Trp Phe Glu Val Gln Asn Ser Asn Asp Thr Glu
            185             190                 195

TTG AAG GAG TTC AAG ATT CCA CAA AAT GCT TAT AGG GCT GTG TTG     630
Leu Lys Glu Phe Lys Ile Pro Gln Asn Ala Tyr Arg Ala Val Leu
            200             205                 210

GAG GTG TAT GTT TCA TTT CAC GAG AAT GAT GAA TTT TGG TAT TCA     675
Glu Val Tyr Val Ser Phe His Glu Asn Asp Glu Phe Trp Tyr Ser
            215             220                 225

AAT CTT CCT AAT GAG TAC ATA GCT GCA AAC AAC CTT AGC GGT ACA     720
Asn Leu Pro Asn Glu Tyr Ile Ala Ala Asn Asn Leu Ser Gly Thr
            230             235                 240

CCC GGA AAT GGG CCT TTT AGG GAG GTT GTG GTC AGT CTA GAT GGT     765
Pro Gly Asn Gly Pro Phe Arg Glu Val Val Val Ser Leu Asp Gly
            245             250                 255

GAG GTT GTT                                                     774
Glu Val Val
```

( 2 ) INFORMATION FOR SEQ ID NO: 42:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 42:

AAACCATGGG ATCCGAACCG ACTCCGCTGC ATGATACCCC GCCAACTGT     49

( 2 ) INFORMATION FOR SEQ ID NO: 43:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: other nucleic acid (DNA)

( x i ) SEQUENCE DESCRIPTION: SEQ ID NO: 43:

TGGAGAAAGT TTGAGATGGG CAATC     25

ALMOND N-GLYCOSIDASE GENE

FIELD OF THE INVENTION

The present invention relates to an almond N-glycosidase gene and genes associated therewith, which are useful in sugar chain technology such as analyses of structures and functions of sugar chains and glycoproteins. The present invention also relates to vectors in which such genes are integrated, recombinant microorganisms transformed with said vectors, and a process for preparing the almond N-glycosidase using the recombinant microorganisms.

BACKGROUND OF THE INVENTION

Almond N-glycosidase (EC 3.5.1.52) was found by Takahashi et al. at the first time as an enzyme which hydrolyses a β-aspartyl glycosylamin bond of an asparagine-linked type (N-linked type) sugar chain of a glycopeptide [Takahashi et al., Biochemical and Biophysical Research Communications, 76: 1194–1201 (1977)]. This enzyme liberates only asparagine-linked type sugar chains with their roots from various glycoproteins (glycopeptides) existing in biological tissues, cell membranes and so on. In addition, this enzyme has a broad substrate specificity for structures of sugar chains, so that it can liberate any of high mannose type, mixed type and complex type sugar chains. Because of these properties, this enzyme is widely used and very effective in cutting sugar chains out of glycoproteins (glycopeptides) to determine structures of sugar chains, analyses of changes of bioactivities of glycoproteins by removing sugar chains therefrom, or identification of existence of sugar chains in glycoproteins (glycopeptides) and determination of molecular weights of the protein portions from changes of molecular weights thereof by the action of this enzyme.

Firstly, an almond N-glycosidase was partially purified by Takahashi et al., and existence of three types of almond N-glycosidases each of which had different substrate specificity were reported [Biochimica et Biophysica Acta), 657: 457–467 (1981)]. Then, this enzyme was partially purified by Tarentino, and existence of three types of almond N-glycosidases were reported like the report of Takahashi et al. [Journal of Biological Chemistry, 257: 10776–10780 (1982)]. However, unlike the report of Takahashi et al., it was reported that no difference in the substrate specificity was found in these three types of almond N-glycosidases.

In addition, Taga et al. isolated an almond N-glycosidase as a single peptide at the first time [Biochemistry, 23: 815–822 (1984)]. Taga et al. reported that almond glycosidase was a single chain polypeptide, the molecular weight of which was 66,800 on sodium lauryl sulfate-polyacryl-amide gel electrophoresis (SDS-PAGE), and that this protein was a glycoprotein having sugar chains. Also, Taga et al. reported that this enzyme contained proteins which had different charges, and that β-hexosaminidase contaminating in this enzyme could not be removed. Kaliberda, E. Net al. showed that an almond glycosidase was a single chain protein, the molecular weight of which was 71,000 on SDS-PAGE, and that the amino acid sequence of the amino terminal was Ile-Asp-Pro-Arg-Val-Val-Xaa-Ala-Xaa-Leu- (SEQ ID NO: 3) [Bioorganicheskaya Khimiya, 16: 751–758 (1990)].

As described above, it has been reported that almond N-glycosidase is a glycoprotein, and also reported that several types of the enzyme which have different isoelectric points exist, and that the isolated protein is single chain protein.

An almond N-glycosidase purified from an acetone powder extract of almond seeds is commercially available. However, generally, the acetone powder extract of almond seeds contains many kinds of and a large amount of sugar degrading enzymes, so that it is difficult to isolate only an almond N-glycosidase. Consequently, utilization of the enzyme purified from almond seeds is always accompanied with a risk of contamination of the other sugar degrading enzymes. Especially, it is very difficult to obtain a highly purified N-glycosidase protein from viewpoint of the enzyme activity, which can be used in microscale analyses. Moreover, an almond N-glycosidase itself is a glycoprotein having N-linked sugar chains, therefore the utilization of the almond N-glycosidase is accompanied with a risk of contamination of sugar chains from itself.

On the other hand, the structure and the amino acid sequence of this enzyme are unknown. In addition, a process of preparing almond N-glycosidase which has industrial advantages has not been disclosed yet. If the gene of this enzyme is elucidated, it will be possible to produce a highly purified and homogeneous enzyme preparation by genetic engineering, and also possible to produce enzymes without sugar chains which are useful in sugar chain engineering such as analyses of structures and functions of sugar chains and glycoproteins. Also, by the DNA sequence of this enzyme, it will be possible to search genes analogous to the DNA sequence of this enzyme, which are expected to possess similar activities to this enzyme, while the sequences are different from that of this enzyme. Moreover, the amino acid sequence corresponding to this enzyme is useful in preparing an antibody against this enzyme.

OBJECTS OF THE INVENTION

Under these circumstances, the main object of the present invention is to provide an almond N-glycosidase gene, the DNA sequence and the amino acid sequence thereof, and also to provide a process for preparing thereof by gene engineering.

These objects as well as other objects and advantages of the present invention will become apparent to those skilled in the art from the following description with reference to the accompanying drawings.

SUMMARY OF THE INVENTION

Figure 1:
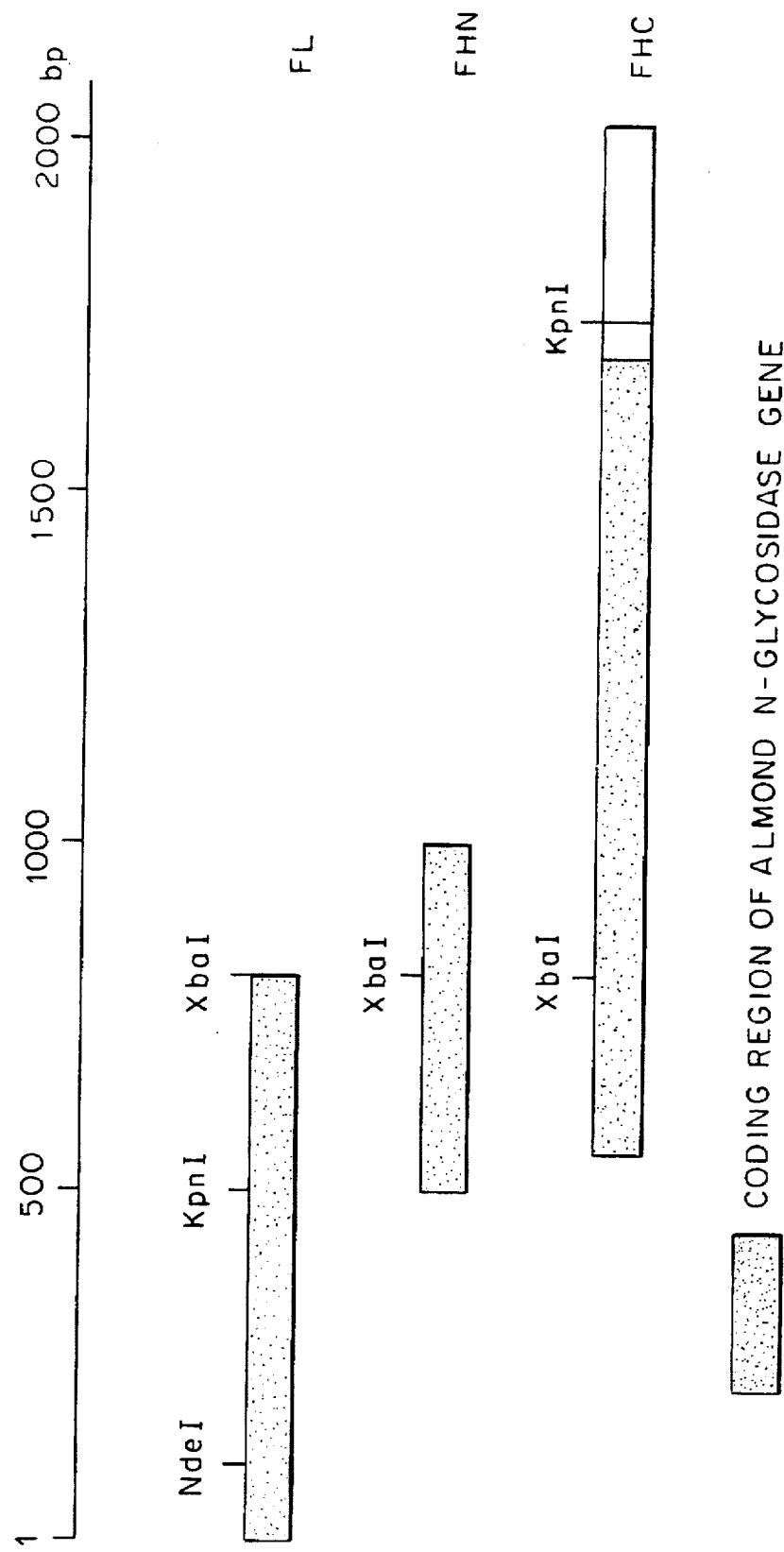
FIG. 1 is restriction maps of FHN, FHC and FL, and the relationship among them.

In one aspect, the present invention provides an isolated almond N-glycosidase gene, in particular, an almond N-glycosidase gene encoding the amino acid sequence described in SEQ ID NO: 1 or a portion thereof which has the almond N-glycosidase activity, especially, an almond N-glycosidase gene containing the DNA sequence described in SEQ ID NO: 2, and N-glycosidase genes which can hybridize to said almond N-glycosidase gene containing DNA sequence described in SEQ ID NO: 2.

In another aspect, the present invention provides a recombinant vector containing said gene of the present invention.

In further aspect, the present invention provides a process for preparing an almond N-glycosidase, comprising culturing the recombinant microorganism transformed with the recombinant vector of the present invention, collecting the almond N-glycosidase from the culture. In particular, the present invention provides a process in which the recombinant microorganism is *Escherichia coli* or a yeast, for example *Schizosaccharomyces pombe*.

DETAILED DESCRIPTION OF THE INVENTION

To obtain the almond N-glycosidase of the present invention, firstly, the almond N-glycosidase in an acetone powder was subjected to various chromatographies to be highly purified.

It was found that the purified almond N-glycosidase protein was composed of a light chain and a heavy chain, the molecular weights of which were 27000 and 60000 on SDS-PAGE, respectively, which are not covalently bonded each other. It has not been shown heretofore in the prior art that an almond N-glycosidase is composed of such two polypeptides. In addition, it has been quite unknown whether they are coded on different genes and expressed individually, or coded on the same gene and generated by a cleavage after translation into proteins.

Therefore, for cloning of a cDNA coding the almond N-glycosidase, unlike the case where an usual single chain polypeptide is cloned, it is necessary to consider the relationship between genes for the two polypeptides as above mentioned. For cloning the cDNA coding the almond N-glycosidase, for example, the following procedure can be used.

Firstly, the amino acid sequences of the portions of the highly purified two polypeptides of the almond N-glycosidase, that is, the light chain and the heavy chain are analyzed. The amino acid sequences of these portions can be determined from N-terminal of the proteins directly by Edman method. Alternatively, the sequences can be determined by hydrolysing the proteins into fragments with a protease such as trypsin and lysyl endopeptidase, isolating and purifying them, then determining individually. On the basis of the amino acid sequences of these portions, synthesized DNAs of appropriate length are prepared according to the fluctuation to be used as primers or probes. Then, RNA is extracted from a tissue abundant in the almond N-glycosidase, for example almond seeds, and poly(A)-RNA is purified therefrom using a carrier such as a latex carrier to which oligo-(dT) is bound. cDNA is synthesized using the poly(A)-RNA as a template by the action of reverse transcriptase. The DNA is inserted into a plasmid or a phage vector, and introduced into a host to make a cDNA library according to a method, for example Okayama-Berg method or Gubler-Hoffmann method.

As for procedures to obtain a cDNA coding the desired almond N-glycosidase, for example the following two procedures can be applied.

One procedure is to screen the cDNA library directly using the DNA previously synthesized as a probe. Alternatively, it is effective to use the DNA fragment as a probe when the portion of the desired cDNA has been obtained. That is, firstly, the library is cultured on plates, and colonies or plaques grown are transferred to nitrocellulose membranes or nylon membranes, then the DNAs are immobilized to the membranes by denaturation. These membranes are incubated in a solution containing the probe DNA labelled with for example $^{32}P$ to form hybrids (hereinafter referred this treatment as hybridization). The incubation temperature is set slightly lower than the Tm (melting temperature) of the probe used. After hybridization, non-specifically adsorbed matters are washed out, and clones hybridized to the probe are identified by a means such as autoradiography. In addition, in this case, when hybridization to the library DNA immobilized to a membrane is carried out using the DNAs corresponding to the partial amino acid sequences of the light chain and the heavy chain, respectively as probes, the relationship between the light chain and the heavy chain will be clarified by whether hybridization to the same clone occurs or not. This operation is repeated until the hybridized clones become a single clone. The cDNA coding the desired protein is inserted into the clone thus obtained.

Another procedure is to amplify the cDNA coding the desired almond N-glycosidase using the cDNA as a template synthesized from the poly(A)-RNA from almond seeds by PCR (polymerase-chain-reaction) method. As the primers which are used, a pair of synthesized DNAs assumed from the partial amino acid sequence of the almond N-glycosidase; the synthesized DNA and a random primer (a mixture of the all sequences); or the synthesized DNA and a primer the sequence of which is known, are exemplified. To use the primers the sequence of which are known, it is necessary to add a region to the terminal of the desired DNA, to which the primers having known sequences can anneal. To add the region, a known method in which DNA ligase is used can be used. The amplification is not always occur by any probe, especially non-specific amplification or no amplification tends to occur because synthesized DNA assumed from the partial amino acid sequence contains mixed sequences, therefore it is necessary to investigate what primers that have been prepared according to what partial amino acid sequence should be used, and what combination of the primers should be used. In addition, it is necessary to select the PCR condition suitable to the primers.

To amplify the desired DNA effectively, it is effective to carry out nested PCR. That is, firstly, PCR is performed among primers which have been prepared, then using the amplified product as a template, the second PCR is performed using primers coding the inner sequences compared with the primers used in the primary PCR. For PCR method, a gene amplifying kit containing Taq polymerase, and an automatic gene amplifying apparatus are available from Takara Shuzo Co., Ltd. The desired DNA region can be amplified using them.

Further, DNA primers are synthesized on the basis of the sequences of the cDNA fragments of the light chain and the heavy chain amplified by PCR. Depending on whether amplification can occur using primers from the heavy chain and the light chain or not, it is clarified whether the light chain and the heavy chain are coded on the same gene or not, in other words, the relationship of the location of the light chain and the heavy chain on the gene is clarified.

The sequence of the cDNA obtained is determined, and identified whether it is the desired gene or not. In case that the clone has been obtained by hybridization, it is cultured, for example in a test tube to extract the plasmid according to a conventional method when the recombinant is *E. coli*. This plasmid is digested by a restriction enzyme to obtain a fragment for insertion. The fragment is subcloned into a vector such as M13 phage vector to determine the sequence by dideoxy method.

When the recombinant is a phage, sequencing can be carried out basically in similar steps. In case that the cDNA has been obtained by PCR method, the amplified DNA is purified by agarose gel electrophoresis, and the terminal is blunt-ended. The DNA is subcloned into a vector such as M13 phage, and the sequence is determined by dideoxy method. As for these experimental methodologies from culture to nucleotide sequencing, see for example T. Maniatis et al., Molecular Cloning. A Laboratory Manual (1982), Cold Spring Harbor Laboratory.

The molecular weight, and the result obtained by the N-terminal analysis of the almond N-glycosidase, the gene structure and the amino acid sequence can be determined by comparing the determined sequence with the partial amino acid sequence. When the cDNA which has been obtained does not contain the coding region of the almond N-glycosidase at all, the whole nucleotide sequence of the coding region can be determined by synthesizing DNA primers on the basis of the nucleotide sequence obtained to amplify the lacking portion by PCR, or by further screening the cDNA library using the fragment of the cDNA obtained as a probe.

To obtain a polypeptide or a protein which has an almond N-glycosidase activity, firstly, the almond N-glycosidase gene is connected with a vector that can express them in a suitable host cell, for example bacteria such as $E\ coli$, $Bacillus\ subtilis$, yeasts, animal cells, insect cells, and plant cells, then the transformation is performed thereby to prepare a recombinant organism. By culturing the recombinant organism, the polypeptide having the almond N-glycosidase can be produced.

Construction of such a vector, and transformation of the host cell using them are preformed by methods known to those skilled in the art. Alternatively, a polypeptide without sugar chain can be expressed by using cells as hosts which do not have an ability of synthesizing sugar chains, for example, procaryotes such as $E.\ coli$ and $Bacillus\ subtilis$, or mutant cells of yeasts, animal calls, insect cells and plant cells, which have lost an ability of synthesizing sugar chains.

The polypeptide or the protein can be accumulated as an insoluble matter (inclusion body), depending on the expression system used. In this case, the activity can be recovered by collecting the insoluble matter, and solubilize it under a mild condition, for example with urea, then removing the denaturating reagent.

The expression can be confirmed by assaying the almond N-glycosidase activity. For example, the assay can be carried out using dabsyl ovomucoid glycopeptide (manufactured by Genzyme) as a substrate according to the manual appended. That is, after incubation the enzyme solution with dabsyl ovomucoid at 37° C., assay of the almond glycosidase activity can be performed by separating and detecting the dabsyl peptide produced by liberation of the sugar chain from the substrate, using reverse phase chromatography and thin layer chromatography.

Alternatively, after labelling the reducing terminal of the sugar chain which has been liberated by pyridylamination, the activity can be assayed by separation and quantification of the labelled sugar chain using high performance liquid chromatography.

To purify a polypeptide or a protein which has an almond glycosidase activity from the transformant, common chromatography techniques can be used. For example, when the cultured cells have been broken and the desired polypeptide has been solubilized, the desired polypeptide expressed can be obtained by subjecting the supernatant of the culture to chromatographies such as hydrophobic, ion exchange and gel filtration. When the expressed product is accumulated as an insoluble matter, the cells are broken, and the precipitation is collected to be solubilized with a denaturating reagent such as urea. Then, the polypeptide or the protein having the desired activity can be obtained after removing the denaturating reagent and refolding.

An example of determination of the structure of the almond N-glycosidase gene is shown below.

Firstly, cDNA for the N-terminal of the heavy chain is amplified by PCR method to determine the nucleotide sequence.

The N-terminal amino acid sequence of the highly purified heavy chain of the almond N-glycosidase protein is determined. The sequence is shown in SEQ ID NO: 4. A sense mixed primer HNT1 (SEQ ID NO: 5) corresponding to the portion of amino acids 3–9, and a sense mixed primer HNT2 (SEQ ID NO: 6) corresponding to the portion of amino acids 8–14 are synthesized by a DNA synthesizer, and purified. Inner partial amino acid sequences are shown in SEQ ID NO: 7 to 14. Anti sense mixed primers are synthesized on the basis of these sequences, and purified.

That is, an anti sense mixed primer HIC1 (SEQ ID NO: 15) corresponding to the region of amino acids 12–19 of the inner sequence of the heavy chain shown in SEQ ID NO: 7, and an anti sense mixed primer HIC2 (SEQ ID NO: 16) and HIC3 (SEQ ID NO: 17) corresponding to the region of amino acids 12–19 and 2–8, respectively, shown in SEQ ID NO: 11 are synthesized.

The first chain of the cDNA is prepared using $d(T)_{20}M4$ (SEQ ID NO: 18) as a primer synthesized by a DNA synthesizer using the mRNA from almond seeds as a template. Using the primers and the first chain of the cDNA, nested PCR is carried out.

The primary PCR is carried out using the first chain of the cDNA as a template, and using three combinations of primers, HNT1 and HIC1, HNT1 and HIC2, and HNT1 and HIC3. Each reaction mixture is named PCR1, PCR2 and PCR3. The secondary PCR is carried out using three reaction mixtures from the primary PCR as templates respectively, and using three combinations of primers to each template, that is, HNT2 and HIC1, HNT2 and HIC2, and HNT2 and HIC3. Each reaction mixture is named PCR-1, PCR1-2, PCR1-3, PCR2-1, PCR2-2, PCR2-3, PCR3-1, PCR3-2 and PCR3-3. A fragment about 500 bp which is specifically amplified N-terminal portion of the heavy chain (FHN) is obtained only from PCR2-2 of the reaction mixtures from the secondary PCR. This FHN is cloned. For the four clones, inserted sequences of the FHN (FHN1-FHN4) are determined. These sequences are shown in SEQ ID NO: 19–22, respectively.

Then, cDNA containing the C-terminal portion of the heavy chain is amplified by PCR method to determine the nucleotide sequence. For this determination, two primers shown in SEQ ID NO: 23 and 24 are designed from the sequences of FHN1–FHN4 which have been already determined, and synthesized by a DNA synthesizer. That is, these two primers are sense primer HI1 and HI2 shown in SEQ ID NO: 23 and SEQ ID NO: 24, which correspond to nucleotides 72–95 and nucleotides 148–164 of FHN1–FHN4, respectively, shown in SEQ ID NO 19–22. Further, a synthesized DNA M13 primer M4 (SEQ ID NO: 25, Takara Shuzo Co., Ltd.) which has the same sequence as nucleotides 1–17 of $d(T)20M_4$ (SEQ ID NO: 18) is used as an anti sense primer. Using these primers and the first chain of the cDNA, nested PCR is carried out.

The primary PCR is carried out using the first chain of the cDNA as a template, and HI1 (SEQ ID NO: 23) and M13 primer M4 (SEQ ID NO: 25) as primers. The secondary PCR is carried out using the reaction mixtures from the primary PCR as templates, and HI2 (SEQ ID NO: 24) and M13 primer M4 (SEQ ID NO: 25) as primers. By the secondary PCR, a DNA fragment of approximately 1.2 Kbp (FHC)

containing the C-terminal portion of the heavy chain which has been amplified specifically. This FHC is cloned. For the four clones, inserted sequences of the FHC (FHC1–FHC4) are determined. The sequences are shown in SEQ ID NO: 26–29.

Then, cDNA containing the full length of the light chain of the almond N-glycosidase is amplified by PCR to determine the nucleotide sequence.

As in the case of the heavy chain, the N-terminal amino acid sequence of the highly purified light chain of the almond N-glycosidase protein is determined. The sequence is shown in SEQ ID NO: 30.

On the basis of the amino acid sequence of the light chain (SEQ ID NO: 30), sense mixed primers shown in SEQ ID NO: 31–34 are designed respectively, and synthesized by a DNA synthesizer, then purified. Also, on the basis of the sequence of the cDNA of the heavy chain previously determined, 10 anti sense mixed primers are designed, and synthesized by a DNA synthesizer, then purified.

That is, sense mixed primers LN1C and LN1T shown in SEQ ID NO: 31 and SEQ ID NO: 32 which correspond to amino acids 1–8 of the N-terminal sequence of the light chain shown in SEQ ID NO: 30; a sense mixed primer LN2 shown in SEQ ID NO: 33 which corresponds amino acids 6–12 thereof; and a primer LN3 shown in SEQ ID NO: 34 which corresponds to amino acids 12–18 thereof are synthesized. In addition, as an anti sense primer, primer HIC4 shown in SEQ ID NO: 35 which corresponds to nucleotides 262–286 of SEQ ID NO: 19–22 and to nucleotides 125–149 of SEQ ID NO: 32–35 is synthesized. Using these primers and the first chain of the cDNA, nested PCR is carried out. When the light chain and the heavy chain exist tandem in this order on the same gene, it is possible that the gene coding the full length of the light chain and the N-terminal portion of the heavy chain is amplified.

The primary PCR is carried out using the first chain of the cDNA as a template, and using three combinations of primers, LN1C and HIC4, LN1T and HIC4, and LN2 and HIC4. Each reaction mixture is named PCR4, PCR5 and PCR6. The secondary PCR is carried out using three reaction mixtures from the primary PCR as templates respectively. To templates PCR4 and PCR5, the secondary PCR is carried out using two combinations 10 of primers, that is, LN2 and HIC4, and LN3 and HIC4. The reaction mixtures are named PCR4-1, PCR4-2, PCR5-1 and PCR5-2, respectively. To a template PCR6, the PCR reaction is carried out using primers LN3 and HIC4, and the reaction mixture named PCR6-1. An amplified DNA fragment of approximately 900 bp containing N-termini of the light chain and the heavy chain (FL) is obtained only from reaction mixtures PCR4-1 and PCR5-2. Therefore, it is thought that the light chain and the heavy chain are coded tandem in this order on the same gene.

Then, FL is cloned. For the six clones, the nucleotide sequences of the FL (FL1–FL6) inserted are determined. The sequences are shown in SEQ ID NO: 36–41, respectively. When no DNA fragment containing the light chain is amplified by the method above mentioned, the relation of the location between the light chain and the heavy chain can be investigated after determination using the similar procedure in the case of the heavy chain.

The relationship among FHN, FHC and FL above described, and the individual restriction maps are shown in FIG. 1. The region coding the almond N-glycosidase is determined by applying the result of the analysis of the amino acid sequence of the almond N-glycosidase to the sequences of FHN, FHC and FL. The nucleotide sequence of the cDNA which can code the almond N-glycosidase is shown in SEQ ID NO: 2, and the amino acid sequence which can be coded by the nucleotide sequence can code is shown SEQ ID NO: 1.

To produce a polypeptide or a protein having an almond N-glycosidase activity, firstly, the DNA coding the almond N-glycosidase is connected with a vector. In this case, either a fragment FL or FHC amplified by PCR, or a synthesized DNA can be used as a DNA coding the almond N-glycosidase. Alternatively, the nucleotide sequence can be selected so that it will fit for the sequence determined by the analysis of the partial amino acid sequence of the almond N-glycosidase. The polypeptide having the almond N-glycosidase activity can be produced by introducing the vector for expression of the almond N-glycosidase thus obtained into a host cell, and culturing the transformed cell. As a host cell, the cell above mentioned can be used. For example, a fission yeast such as Schizosaccharomyces pombe ATCC 38440 can be used. In the examples below, Schizosaccharomyces pombe strain T-1 which is belong to the present applicants and have the same characters as 38400 is used.

Using these genes obtained as probes, all N-glycosidase genes which have slightly different sequences and are expected to have the similar activity can be obtained by hybridization under a stringent condition. As sources of the gene to be hybridized, DNAs and mRNAs obtained from bacteria, fungi, plant and animal cells can be used. For example, as for plants, DNAs and mRNAs obtained from tissues such as seeds and shoots can be used, and as for animals, DNAs and mRNAs obtained from cultured cells and tissues of internal organs can be used.

Examples of plants contain plants of Family Rosaceae such as apricot, plum, peach, cherry and loquat, and plants of different families, for example plants of Family leguminosae such as sword bean, horse bean, liquorice, wisteria, pea, clara, and plants of Family Brassicaceae and Family cucurbitaceae, and Family Solanaceae.

Such a stringent condition is, for example, as follows: DNA which is immobilized to a nylon membrane is hybridized to a probe in a solution containing 6×SSC (1×SSC consists of sodium chloride 8.7 g, and sodium citrate 4.41 g in 1 L of water), 1% sodium lauryl sulfate, 100 μg/ml salmon sperm DNA, and 5×Denhart's (containing 0.1% bovine serum albumin, 0.1% polyvinylpyrrolidone and 0.1% Ficoll), at 65° C. for 20 hours.

To obtain the desired gene coding the N-glycosidase by hybridization, for example, following method can be applied: firstly, chromosomal DNA obtained from the desired gene source, or cDNA prepared from mRNA by reverse transcriptase is connected to a plasmid or a phage vector according to a conventional method to prepare a library. The library is cultured on plates. Grown colonies or plaques are transferred 10 onto a nitrocellulose or a nylon membrane, and the DNAs are immobilized to the membrane by denaturation. This membrane is incubated in a solution containing a probe previously labelled with for example $^{32}P$ to hybridize the DNA on the membrane to the probe. A Probe used include a gene coding an amino acid sequence described SEQ ID NO: 1 or a portion thereof. For example, a gene described in SEQ ID NO: 2 or a portion thereof can be used. For example, a gene coding an amino acid sequence described in SEQ ID NO: 4, 7, 8, 9, 10, 11, 12, 13, 14, 19, 20, 21, 22, 26, 27, 28, 29, 30, 36, 37, 38, 39, 40 or 41, or a portion thereof can be used. For example, hybridization between DNA immobilized to a membrane and a probe is carried out in a solution containing 6×SSC, 1% sodium lauryl sulfate, 100 μg/ml salmon sperm DNA, and 5×Denhart's (containing bovine serum albumin, polyvinylpyrrolidone, Ficoll, each 0.1%) at 65° C. for 20 hours. After hybridization, non-specifically adsorbed matters are washed out, and hybridized clones are identified by a means such as autoradiography. This operation is repeated until the hybridized clones become a single clone. The gene coding the desired protein is inserted in the clone thus obtained.

The gene obtained is sequenced, for example as described below and identified to code the desired N-glycosidase.

To determine the nucleotide sequence, in case that the clone has been obtained by hybridization, it is cultured, for example in a test tube to extract the plasmid according to a conventional method when the recombinant is E. coli. This plasmid is digested by a restriction enzyme to obtain a fragment for insertion. The fragment is subcloned into a vector such as M13 phage vector to determine the sequence by dideoxy method. When the recombinant is a phage, sequencing can be carried out basically in similar steps. These experimental methods from culture to nucleotide sequencing are described in, for example, T. Maniatis et al., Molecular Cloning A Laboratory Manual (1982) Cold Spring Harbor Laboratory.

To identify whether the gene obtained codes the desired almond N-glycosidase, the structure and the amino acid sequence can be known, by comparing the nucleotide sequence determined with the almond N-glycosidase gene of the present invention and with the amino acid sequence described in SEQ ID NO: 1.

When the gene which has been obtained does not contain the coding region of the N-glycosidase at all, the whole nucleotide sequence of the coding region which hybridizes to the almond N-glycosidase gene of the present invention can be determined by synthesizing DNA primers on the basis of the nucleotide sequence obtained to amplify the lacking portion by PCR, or by further screening the cDNA library using the fragment of the cDNA obtained as a probe.

To obtain a polypeptide having a N-glycosidase activity using genetic engineering, firstly, according to a standard method, the almond N-glycosidase gene is connected with a vector that can express them in a suitable host cell, for example bacteria such as E coli, Bacillus subtilis, yeasts, mammalian cells, insect cells, and plant cells. The recombinant vector is introduced into a host cell to prepare a recombinant cell. By culturing the recombinant cell, a polypeptide having a N-glycosidase activity can be produced. Alternatively, a polypeptide without sugar chain can be expressed by using cells as hosts which do not have an ability of synthesizing sugar chains, for example, procaryotes such as E. coli and Bacillus subtilis, or mutant cells of yeasts, mammalian cells, insect cells and plant cells, which have lost an ability of synthesizing sugar chains.

The polypeptide or the protein can be accumulated as an insoluble matter (inclusion body), depending on the expression system used. In this case, the activity can be recovered by collecting the insoluble matter, and solubilize it under a mild condition, for example with urea, then removing the denaturating reagent. The expression can be confirmed by assaying the almond N-glycosidase activity. For example, the assay can be carried out using dabsyl ovomucoid glycopeptide (manufactured by Genzyme) as a substrate according to the manual appended. That is, after incubation the enzyme solution with dabsyl ovomucoid at 37° C., assay of the almond glycosidase activity can be performed by separating and detecting the dabsyl peptide produced by liberation of the sugar chain from the substrate, using reverse phase chromatography and thin layer chromatography.

To purify a polypeptide or a protein which has an almond N-glycosidase activity from the transformant, common chromatography techniques can be used. For example, when the cultured cells have been broken and the desired polypeptide has been solubilized, the desired polypeptide expressed can be obtained by subjecting the supernatant of the culture to chromatographies such as hydrophobic, ion exchange and gel filtration. When the expressed product is accumulated as an insoluble matter, the cells are broken, and the precipitation is collected to be solubilized with a denaturating reagent such as urea. Then, the polypeptide or the protein having the desired activity can be obtained after removing the denaturating reagent and refolding.

Thus, According to the present invention, a primary structure of an almond N-glycosidase gene is elucidated, and it is possible to provide a procedure of genetic engineering for preparing it. Also, similar N-glycosidase genes are provided using the genes of the present invention. Moreover, by said procedure of genetic engineering, it is possible to produce an almond N-glycosidase having no sugar chain.

The following Examples further illustrate the present invention in detail. However, they are not to construed to limit the scope of the present invention.

EXAMPLE 1

Cloning of cDNA of the Almond N-Glycosidase (1-1) Purification of the Almond N-Glycosidase Two kg of a commercial almond meal (manufactured by Sigma) was emerged in 10 mM Bis-Tris buffer solution (pH 6.8) containing 2 mM phenyl metanesulfonyl fluoride (PMSF) and 1 mM 1,2-epoxy-3-(p-nitrophenoxy)propane (EPNP) with stirring for 20 hour at 5° C., then the mixture was filtered through a filter cloth, and centrifuged to obtain a supernatant. After precipitating by adding ammonium sulfate to the supernatant to 80% saturation, dialysis of the precipitation was performed against 10 mM Mes buffer solution (pH 6.8). The dialyzed solution was applied to a column of an ion exchange resin DE52 (manufactured by Whatman) equilibrated with 10 mM Mes buffer solution (pH 6.8). The wash-through fraction with the same buffer solution was subjected to ion exchange chromatography on CM-Sepharose CL-6B (manufactured by Pharmacia), and eluted with a gradient of potassium chloride (0 to 0.5M). The active fraction eluted was dialyzed against 10 mM MOPS buffer solution (pH 7.0). A precipitation which generated during the dialysis was removed by centrifugation. The dialyzed solution was subjected to ion exchange column chromatography on Mono S (manufactured by Pharmacia), and eluted with a gradient of potassium chloride (0 to 0.4M). The active fraction eluted was dialyzed against 10 mM Tris buffer solution (pH 8.8). The dialyzed solution was subjected to ion exchange column chromatography on Mono Q (manufactured by Pharmacia), and eluted with a gradient of potassium chloride (0 to 0.5M). The active fraction eluted was diluted four times with 10 mM Tris buffer solution (pH 8.8). The diluted active fraction was again subjected to ion exchange column chromatography on Mono Q, and eluted with a gradient of potassium chloride (0 to 0.5M). After concentration of the active fraction eluted by ultrafiltration using Centricon 10 (manufactured by Amicon) of exclusive molecular weight 10000, the concentrate was subjected to gel permeation column chromatography on Superrose 12HR (manufactured by Pharmacia), and eluted with 10 mM Tris buffer solution (pH 8.8) containing 0.1M sodium chloride to obtain the active fraction. By above operations, the almond N-glycosidase was purified to a homogeneous protein. The purified almond N-glycosidase was composed of two polypeptide chains, a light chain and a heavy chain, which showed molecular weights 27000 and 60000 on SDS-PAGE, respectively.

(1-2) Analysis of the N-terminal Amino Acid Sequence and the Inner Partial Amino Acid Sequence After dissociating the purified almond N-glycosidase to a light chain and a heavy chain by SDS-PAGE, these polypeptides were electrophoretically blotted (electroblotted) to a polyvinylidene difluoride (PVDF) membrane using Sartoblot II (manufactured by Sartorius), and sections containing the light chain and the heavy chain on the membrane were cut out separately to obtain samples for determination of the N-terminal amino acid sequences. The amino acid sequences of the samples prepared were determined from the N-terminal one after another by Edman method using a gas phase peptide sequencer (Model 477, manufactured by Applied Biosystem). The N-terminal amino acid sequence of the heavy chain obtained is shown in SEQ ID NO: 4, and that of the light chain is shown in SEQ ID NO: 30.

Determination of the inner amino acid sequence of the heavy chains was carried out as described below.

Firstly, the purified almond N-glycosidase as a sample was subjected to HPLC using an Asahipack C4-P50 column (manufactured by Asahi Kasei). By elution with a gradient of distilled water to acetonitrile containing 0.1% TFA, 500 pmol of the heavy chain was taken out, and solidified in a small sample tube under a reduced pressure. Then, the small sample tube containing the heavy chain was inserted into a test tube containing pyridine 5 µl, 4-vinylpyridine 1 µl, tributyl phosphine 1 µl, and distilled water 5 µl, and the test tube was sealed under vacuum. Then, by heating at 100° for 5 minutes, cysteine residues in the heavy chain was pyridylethylated under gas phase. The heavy chain thus S-pyridylethylated was dissolved in 50 µl of 10 mM Tris buffer solution (pH 9.0). One pmol of lysyl endopeptidase (manufactured by PIERCE) was added to the mixture, and digestion was carried out at 37° C. for 7 hours. Then, the digested sample was subjected to HPLC using a Cosmosil 5C18AR column (manufactured by Nakarai). Purification of the peptide fragment was carried out by eluting with a gradient of distilled water containing 0.1% TFA to acetonitrile containing 0.05% TFA.

The peptide fragments obtained were analyzed by a gas phase peptide sequencer (Model 477, manufactured by Applied Biosystems) to determine the inner amino acid sequence of the heavy chain shown in SEQ ID NO: 7–14.

(1-3) Extraction of mRNA and Synthesis of cDNA

Almond fruits were harvested, and soon freezed at −80° C. to be stored. Seven stored fruits were broken in frozen state, and the seeds were separated from the pulp. The seeds were milled with liquid nitrogen in a mortar, and the whole RNA was extracted using a RNA extraction kit (manufactured by Amersham) according to the manual to obtain 176 µg of whole RNA. The whole RNA was treated with Oligotex dT 30 (manufactured by Takara Shuzo Co., Ltd.) to obtain 2.9 µg of poly(A)RNA. Using 0.7 µg of this poly(A)RNA as a template and using a cDNA synthesis kit (manufactured by Amersham), for first strand cDNA synthesis, priming was accomplished by d(T)$_{20}$M4 shown in SEQ ID NO: 18.

(1-4) Amplification of the N-terminal of the Heavy Chain by PCR

Primers shown in SEQ ID NO: 5, 6 and 15–17 were designed from the N-terminal amino acid sequence and the inner amino acid sequence of the heavy chain determined in Example 1 (1-2), and synthesized by a DNA synthesizer (Model 394, manufactured by Applied Biosystems).

That is, sense mixed primers HNT1 and HNT2 shown SEQ ID NO: 5 and 6 respectively which correspond to amino acids 3–9 and 8–14 respectively of the N-terminal sequence of the heavy chain shown in SEQ ID NO: 4; an anti sense mixed primer HIC1 shown in SEQ ID NO: 15 which corresponds to amino acids 12–19 of the inner sequence of the heavy chain shown in SEQ ID NO: 7; and anti sense mixed primers HIC2 and HIC3 shown in SEQ ID NO: 16 and 17 respectively which correspond to amino acids 12–19 and 2–8 respectively of the inner sequence of the heavy chain shown in SEQ ID NO: 11 were synthesized. Using these primers, nested PCR reaction was carried out.

The primary PCR was carried out in a mixture, which was prepared by taking 1/20 of the cDNA (1 µl) as a template prepared in Example 1 (1-3) into a 0.5 ml tube for PCR, and adding 10 µl of 10× buffer solution contained in Gene-Amp™ PCR reagent kit (manufactured by Takara Shuzo Co., Ltd.), 16 µl of 1.25 mM dNTP mixture, 1 µl of the sense mixed primer (500 pmol/µl), 1 µl of the anti sense mixed primer (500 pmol/µl), 0.5 µl of 5 units/µl AmpliTaq™, and sterilized water to 100 µl. After overlaying 100 µl of mineral oil (manufactured by Sigma) on this solution, PCR reaction was carried out by an automatic gene amplifier (Thermal cycler, manufactured by Takara Shuzo Co., Ltd.). The amplification was performed in using the program set to denaturate at 94° C. or 2 minutes for a cycle, denature at 94° C. for 1 minute, anneal at 55° C. for 2 minutes and extend at 55° C. for 2 minutes for a total of 30 cycles, then elongate at 60° C. for 7 minutes. In this case, the PCR was carried out using three combinations of a sense mixed primer and an anti sense mixed primer, that is, HNT1 and HIC1, HNT1 and HIC2, and HNT1 and HIC3. These reaction mixtures were named PCR1, PCR2 and PCR3, respectively.

Then, using these reaction mixtures, the secondary PCR was carried out. Using these three reaction mixtures as templates (each 1 µl), the secondary PCR was carried out under the same conditions as the primary PCR using three combinations of a sense mixed primer and an anti sense mixed primer, that is, HNT2 and HIC1, HNT2 and HIC2, and HNT2 and HIC3. The reaction mixtures obtained were named PCR1-1, PCR1-2, PCR1-3, PCR2-1, PCR2-2, PCR2-3, PCR3-1, PCR3-2 and PCR3-3. After reactions, upper mineral oil was removed, then 5 µl of each reaction mixture was resolved on an agarose gel electrophoresis, and visualized by ethydium bromide fluorescence to confirm the products amplified. From the results, a specific amplification of DNA was found in PCR2-2. This amplified DNA fragment of approximately 500 bp was named FHN.

(1-5) Determination of the Nucleotide Sequence of the N-Terminal Portion of the Heavy Chain The remainder of the reaction mixture from Example 1 (1-4) was concentrated by precipitation with ethanol, and the whole precipitation was subjected to agarose gel electrophoresis. After staining with ethydium bromide, a section containing the desired FHN DNA fragment was cut out from the gel under ultraviolet, and the DNA fragment was extracted and purified from the portion using EASYTRAP™ (manufactured by Takara Shuzo Co., Ltd.). Then, after phosphorylation of the 5'-terminal thereof using MEGALABEL™ (manufactured by Takara Shuzo Co., Ltd.), it was blunt-ended using DNA Blunting Kit (manufactured by Takara Shuzo Co., Ltd.), and ligated to the Hinc II-digested pUC19 plasmid using DNA Ligation Kit (manufactured by Takara Shuzo Co., Ltd.). Using an aliquot of the ligation reaction mixture, E. coli strain JM109 was transformed to obtain a recombinant E. coli containing the FHN DNA fragment amplified by PCR in the Hinc II site.

Four clones of the recombinant E. coli obtained were cultured in liquid medium, and the plasmid DNAs were prepared by alkaline lysis method. These four inserted fragments in the plasmids were named FHN1, FHN2, FHN3 and FHN4, and the whole sequences thereof were determined by dideoxy method. Each sequence is shown in SEQ ID NO: 19–22. In each sequence, nucleotides 1–20 was from the sense mixed primer HNT2, nucleotides 466–485 was from the anti sense mixed primer HIC2. When the whole nucleotide sequences of the inserted fragments were translated into amino acids, they coincided well with the N-terminal sequence (SEQ ID NO: 4) and the inner sequence (SEQ ID NO: 11) of the heavy chain. However, among the nucleotide sequences of FHN1 to FHN4, differences were found at nucleotides 22, 36, 39, 170 and 245.

(1-6) Amplification of the cDNA of the C-Terminal Portion of the Heavy Chain by PCR Primers shown in SEQ ID NO: 23 and 24 were designed from the N-terminal portion of the heavy chain determined, and synthesized by a DNA synthesizer. That is, sense primers HI1 and HI2, shown in SEQ ID NO 23 and 24 respectively which correspond to nucleotides 72–95 and 148–164 of FHN1 to FHN4 shown in SEQ ID NO: 19–22, were synthesized. Also, PCR was carried out using a synthesized DNA M13 primer M4 (SEQ ID NO: 25) as an anti sense primer which has the same nucleotide sequence as nucleotides 1–17 of $d(T)_{20}M4$ (SEQ ID NO: 18). Using these primers, nested PCR was carried out.

Firstly, the primary PCR was carried out as follows: 16 µl of 1.25 mMdNTP mixture, 1 µl of 10 pmol/µl HI1, and 1 µl of 100 pmol/µl M13 primer M40 were taken into a 0.5 ml tube for PCR, and a pellet of AmpliWax™ PCR Gem100 (manufactured by Takara Shuzo Co., Ltd.) was added thereto, then the mixture was incubated at 80° C. for 6 minutes. Then, by incubating the mixture at 25° C. for 2 minutes to form a wax layer. Further, after adding 1/20 (1 µl) of the cDNA prepared in Example 1 (1-3) as a template, 0.5 µl of 5 units/µl AmpliTaq™, 10 µl of 10 X buffer solution for amplification, and 70.5 µl of sterilized water, PCR was carried out by an automatic gene amplifier (thermal cycler) (hereinafter, referred this PCR method as Hot Start PCR method). The reaction was carried out as follows: after melting the wax and mixing the upper and lower layers at 94° C. for 2 minutes, a cycle, which consists of denaturation at 94° C. for 1.5 minutes, annealing of the primer at 55° C. for 1 minute, extension at 72° C. for 2.5 minutes, was repeated 30 times, then further elongation at 60° C. for 7 minutes and solidification of the wax at 4° C. were carried out.

The secondary PCR was carried out under the same conditions as the primary PCR using 1 µl of the reaction mixture from the primary PCR and 1 µl of 100 pmol/µl HI2. After the reaction, 5 µl of the reaction mixture was subjected to agarose gel electrophoresis, and the DNAs were stained with ethydium bromide. A band of the approximately 1.2 Kbp cDNA of the almond N-glycosidase which contains the C-terminal portion of the heavy chain amplified specifically was confirmed. This DNA fragment amplified by PCR was named FHC.

(1-7) Determination of the Nucleotide Sequence of the C-Terminal Portion of the Heavy Chain The remainder of the reaction mixture from Example 1 (1-6) was purified as Example 1 (1-4), and ligated to the Hinc II-digested pUC19 plasmid. By this plasmid, E. coli strain JM109 was transformed to obtain a recombinant E. coli containing FHC DNA fragment amplified by PCR in the Hinc II site.

Four clones of the recombinant E. coli obtained were cultured in liquid medium, the plasmid DNAs were prepared by alkali lysis method. These four fragments inserted in the plasmids were named FHC1, FHC2, FHC3 and FHC4, respectively. To determine the whole nucleotide sequences from these inserted fragments, each plasmid was digested by restriction endonucleases Pst I and Hind III. After subjecting the DNA fragments obtained to agarose gel electrophoresis, the DNA fragments were ligated to the Pst I or Hind III-digested M13P18 or M13P19, and E. coli JM109 were transformed with the ligation mixtures. Further, the recombinant E. coli were cultured to prepare ssDNA. These DNAs were sequenced by dideoxy method, and by joining these sequences the whole nucleotide sequences of FHC1, FHC2, FHC3 and FHC4 were determined. Each sequence is shown in SEQ ID NO: 26–29. When the whole nucleotide sequences of the inserted fragments were translated into amino acid sequences, these fragments contained coding region of the C-terminal and a non-translated region of the heavy chain, and coincided well with the inner amino acid sequences of the heavy chain (SEQ ID NO 7–14). Comparing the nucleotide sequences of FHC1 to FHC4 one another, FHC1 has the same nucleotide sequence as FHC3, and the others have differences in nucleotides 98, 464, 500, 794, 823, 877, 884 and 891.

The 139 bp of the 5'-termini of FHC1 to FHC 4 overlapped the 139 bp of the 3'-termini of FHN1 to FHN4. Thus, the whole sequence of the heavy chain cDNA was determined by FHN1 to FHN4 and FHC1 to FHC4.

(1-8) Amplification of the cDNA of the Light Chain

Sense mixed primers shown in SEQ ID NO: 31–34 were designed from the N-terminal partial DNA sequence of the light chain determined in Example 1 (1-2), and anti sense primers were designed from the cDNA sequence of the heavy chain determined in Example 1 (1-2) and (1-3). These primers were synthesized by a DNA synthesizer and purified. That is, as sense mixed primers, primers LN1C and LN1T shown in SEQ ID NO: 31–32 respectively which correspond to the amino acids 1–8 of the N-terminal sequence of the light chain; primer LN2 shown in SEQ ID NO: 33 which corresponds to amino acids 6–12; and primer LN3 shown in SEQ ID NO: 34 which corresponds to amino acids 12–18 were synthesized. Also, as an anti sense primer, primer HIC4 shown in SEQ ID NO: 35 which corresponds to nucleotides 262–286 of SEQ ID NO: 19–22 and nucleotides 125–149 of SEQ ID NO: 26–29 was synthesized. Using these primers, nested PCR was carried put.

According to hot start PCR above described, amplification by the primary PCR was carried out using 1/20 (1 µl) of the cDNA as a template prepared in Example 1 (1-3). The reaction was conducted under following conditions: after melting the wax and mixing the upper and lower layers at 94° C. for 2 minutes, a cycle, which consists of denaturation at 94° C. for 1 minute, annealing of the primer at 55° C. for 1 minute, extension at 72° C. for 2.5 minutes, was repeated 30 times, then further elongation at 60° C. for 7 minutes and solidification of the wax at 4° C. were carried out. In this case, using three combinations of sense mixed primers and an anti sense primer, LN1C and HIC4, LN1T and HIC4, and LN2 and HIC4, the PCR was carried out. The reaction mixtures were named PCR4, PCR5 and PCR6, respectively.

Then, the secondary PCR was carried out using these three reaction mixtures (each 1 μl) as templates. To templates PCR4 and PCR5, using two combinations of a sense mixed primer and an anti sense mixed primers, that is, LN2 and HIC4, and LN3 and HIC4, and To PCR6, using a combination of LN3 and HIC4 the PCR was carried out under the same conditions as the primary PCR. The reaction mixtures were named PCR4-1, PCR4-2, PCR5-1, PCR5-2 and PCR6-1. 5 μl of the each reaction mixture was subjected to agarose gel electrophoresis, and the DNA were stained with ethydium bromide to identify the products amplified. From the results, amplification of the specific DNA of the same size was found in PCR4-1 and PCR5-1. This amplified DNA fragment of about 900 bp was named FL.

(1-9) Determination of the cDNA Nucleotide Sequence of the Light Chain

After concentration of the whole reminder of the PCR by ethanol precipitation, the concentrate was subjected to agarose gel electrophoresis to isolate fragment FL. Fragment FL was phosphorylated at the 5'-terminal and blunt-ended, then ligated with the Hinc II-digested pUC19 plasmid. Using an aliquot of the ligation reaction mixture, E. coli strain M109 was transformed to obtain a recombinant E. coli containing FL DNA fragment amplified by PCR in the HincII site.

Six clones of the recombinant E. coli were cultured in liquid medium, and plasmid DNAs were prepared by alkali lysis method. These six inserts in the plasmid DNA were named FL1, FL2, FL3, FL4, FL5 and FL6, respectively.

In order to determine the whole nucleotide sequences of these inserts, a plasmid which lacked an EcoRI fragment of about 380 bp was prepared after digestion of each plasmid by a restriction enzyme Eco RI. Also, a plasmid lacking a fragment of about 220 bp was prepared by a restriction enzyme Pst I. These plasmids were sequenced by dideoxy method, and these sequences were connected together to determine the whole nucleotide sequences of FL1, FL2, FL3, FL4, FL5 and FL6. Each sequence is shown SEQ ID NO: 36–41.

Nucleotides 1–20 in sequences of FL1–FL6 (SEQ ID NO: 36–41) was the sequence from the sense mixed primer LN2 (SEQ ID NO: 33). Nucleotides 499–774, and nucleotides 626–774 coincided well with nucleotides 1–276 of the PCR fragment FHN1–FHN4 (SEQ ID NO: 19–22) of the N-terminal portion of the heavy chain, and with nucleotides 1–149 of the PCR fragment FHC1–FHC4 (SEQ ID NO: 26–29) of the N-terminal portion of the heavy chain, respectively. These relationships are shown in FIG. 1. Further, when the whole nucleotide sequences of FL1–FL6 (SEQ ID NO: 36–41) were translated into amino acid sequences, it was found that they contained a sequence coinciding well with the N-terminal sequence of the light chain (SEQ ID NO: 30) and the N-terminal sequence of the heavy chain (SEQ ID NO: 4) determined in Example 1 (1-2). Thus, it was found that the amino acid sequences of the light chain and the heavy chain were coded in the same frame on a cDNA. By comparing with FL1–FL6 (SEQ ID NO: 36–41) one another, it was found that FL1 and FL3, and FL4 and FL6 contained the same nucleotide sequences, respectively, and that the others were different at nucleotides 205, 439, 520 and 723 one another.

EXAMPLE 2

Construction of a Plasmid Expressing the Almond N-Glycosidase Polypeptide (2-1) Preparation of a DNA Fragment Coding a Mature N-Terminal Polypeptide of the Almond N-Glycosidase Fragment FL which codes the N-terminal portion of the heavy chain lacks nucleotide sequences corresponding to LN1C (SEQ ID NO:31) and LN1T (SEQ ID NO:32) used as primers in the primary amplification by PCR. Fragments which compensate these portions were prepared by PCR.

An amino acid sequence of the light chain determined in Example 1 (1-2) and (1-9), a sense primer ANGNs (SEQ ID NO: 42) from the nucleotide sequence of fragment FL, and an anti sense primer ANGNa (SEQ ID NO: 43) were designed, and synthesized by a DNA synthesizer to be purified. The sense primer ANGNs (SEQ ID NO: 42) contains nucleotides 1–20 of FL1 shown in SEQ ID NO: 36 in its nucleotides 30–49, which corresponds to the N-terminal of the heavy chain (amino acids 6–12 in the amino acid sequence) shown in SEQ ID NO: 30. In addition, the sense primer ANGNs (SEQ ID NO: 42) is a synthesized DNA which contains a nucleotide sequence corresponding to amino acids 1–5 of the N-terminal amino acid sequence of the light chain (SEQ ID NO: 30) in its nucleotides 15–29, and further contains recognition sequences for Nco I and Bam HI in its nucleotides 1–14.

The anti sense primer (SEQ ID NO:43) is a synthesized DNA which contains a sequence complementary to nucleotides 148–172 of FL1 shown in SEQ ID NO:36.

The amplification by PCR was carried out according to hot start PCR method above described, using 100 pmol of the sense primer ANGNs, 100 pmol of the anti sense primer ANGNa, and 10 ng of the plasmid containing FL1 obtained in Example 1 (1-9). The reaction was conducted under following conditions: after melting the wax and mixing the upper and lower layers at 94° C. for 2 minutes, a cycle, which consists of denaturation at 94° C. for 1 minute, annealing of the primer at 55° C. for 1 minute, extension at 72° C. for 1 minute, was repeated 25 times, then further elongation at 60° C. for 7 minutes and solidification of the wax at 4° C. were carried out. After concentration of the whole reaction mixture by ethanol precipitation, agarose gel electrophoresis was carried out. Then, a DNA fragment of about 200 bp was extracted from the gel and purified. This fragment was digested by restriction enzymes Nco I and Xba I, then subjected to agarose gel electrophoresis again to cut out a portion of the gel containing a DNA fragment ANGN of about 140 bp, and the fragment was extracted from the gel and purified.

Figure 2:
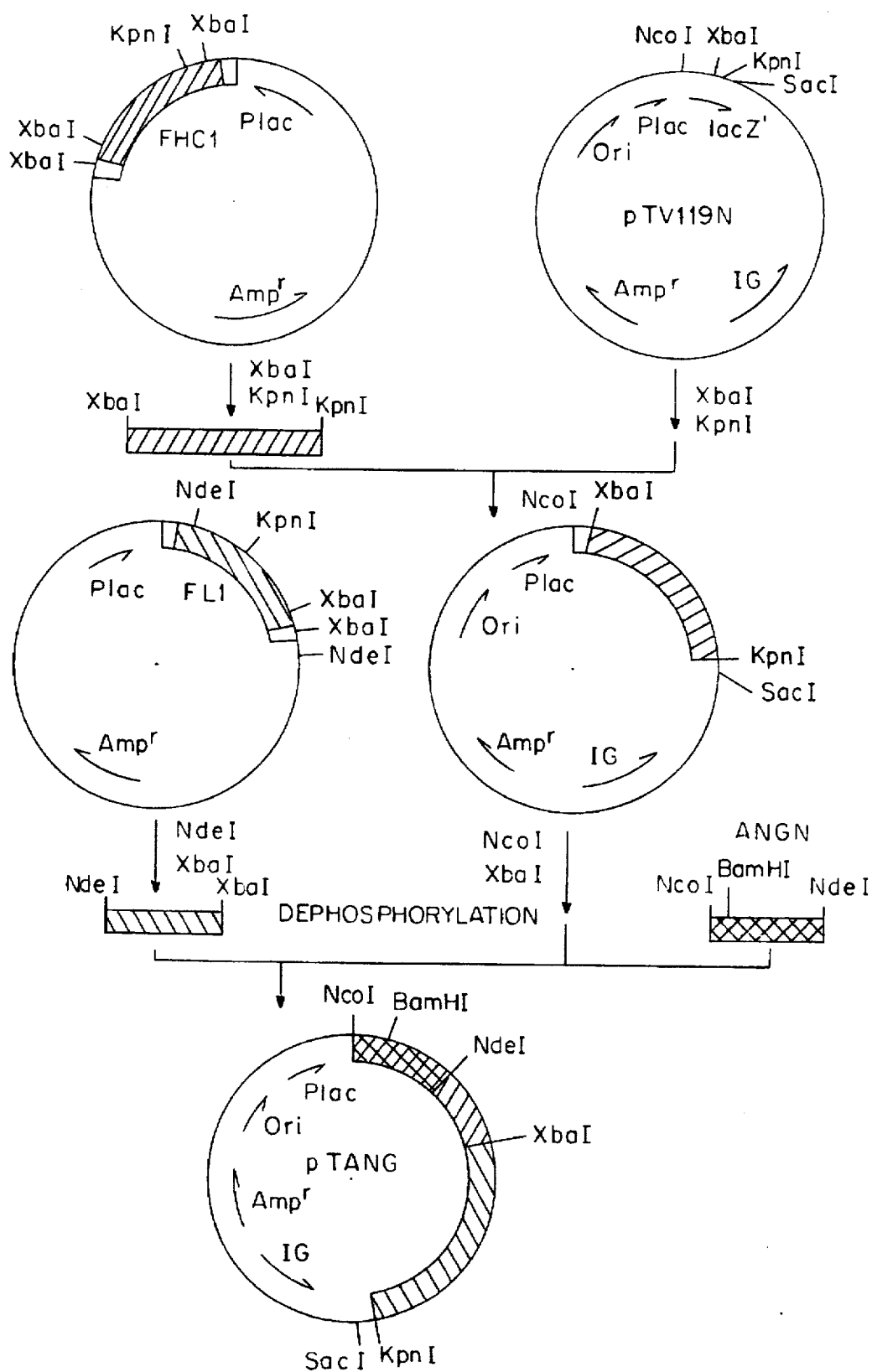
FIG. 2 is a restriction map of plasmid pTANG, and the process of construction thereof.
Figure 3:
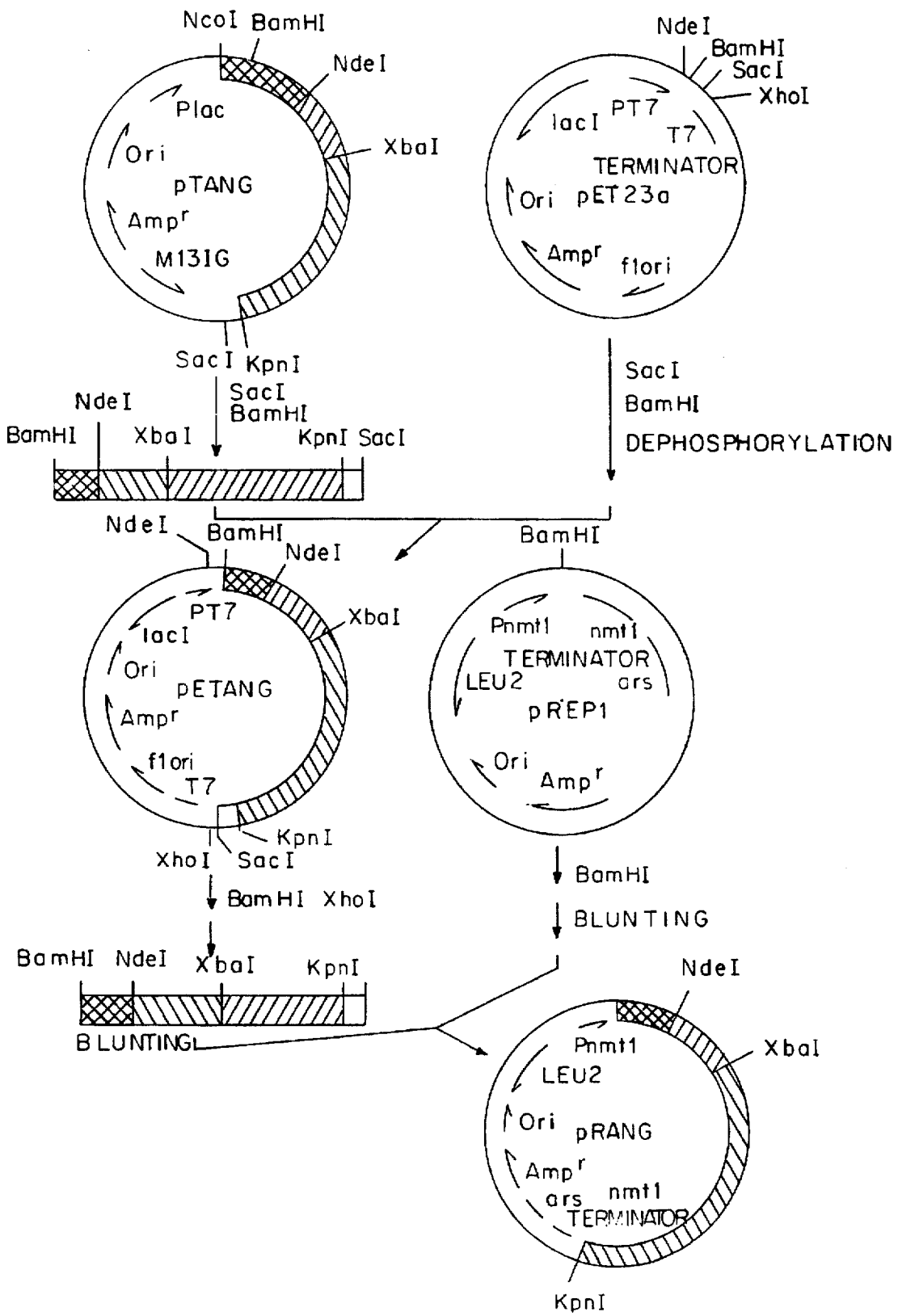
FIG. 3 is a restriction map of plasmid pRANG, and the process of construction thereof.

(2-2) Construction of an Expression Vector for Fission Yeast Schizosaccharomyces pombe The plasmid DNA containing FHC1 (SEQ ID NO: 26) obtained in Example 1 (1-7) was digested by restriction enzymes Xba I and Kpn I, and agarose gel electrophoresis was conducted to cut out a portion of the gel containing a fragment FHC1-Xba I/Kpn I of about 1 kbp. This fragment was extracted from the gel and purified. This fragment was inserted to a Xba I-Kpn I site of a plasmid pTV1119N (manufactured by Takara Shuzo Co., Ltd.) to obtain a plasmid pTANG-HC. The plasmid containing FL1 (SEQ ID NO: 36) obtained in Example 1 (1-9) was digested by restriction enzymes Nde I and Xba I. Agarose gel electrophoresis was conducted, and a portion of the gel containing a fragment FL1-Nde I/Xba I of about 660 bp was cut out, and the fragment was extracted from the gel. A plasmid obtained by digesting pTANG-HC by restriction enzymes Nco I and Xba I and dephosphorylating it by alkali phosphatase BAP C75 (manufactured by Takara Shuzo Co., Ltd.), fragment FL1-Nde I/Xba I, and fragment ANGN obtained in Example 2 (2-1) were ligated together to obtain a plasmid pTANG (see FIG. 2). Further, pTANG was digested by restriction enzymes SacI and BamHI, and agarose gel electrophoresis was conducted. A portion of the gel, which contained a fragment TANG-SacI/BamHI of about 1.6 kbp containing from the mature N-terminal of the almond N-glycosidase gene to the whole length thereof, was cut out, and the fragment was extracted from the gel. This fragment TANG-Sac I/Bam HI and a plasmid pET23a (manufactured by Novagen) were digested by Sac I and Bam HI, and then dephosphorylated. By ligation of these fragments, a plasmid pETANG was obtained. pETANG was digested by restriction enzymes Bam HI and Xho I, then blunted by a DNA blunting kit. Agarose gel electrophoresis was conducted to obtain a fragment ETANG Bam HI-Xho I of about 1.8 kbp. This fragment was inserted into an expression vector pREP1 for *Schizosaccharomyces pombe* [K. Maundrell et al., the Journal of Biological Chemistry, 265: 10857–10864 (1990)]. Plasmid pREP1 is a shuttle vector which contains an ampicillin resistant marker, a yeast resistant marker LEU2, a *Schizosaccharomyces pombe* autonomous replication sequence ars, and a promotor nmt 1 which is induced by lack of thiamine. After digestion of plasmid pREP1 by a restriction enzyme Bam HI, the digested plasmid was blunt-ended by a DNA blunting kit. Fragment ETANG Bam HI-Xho I was introduced into the blunted fragment to transform *E. coli* strain HB101. Plasmid was prepared from the recombinant, and a plasmid, which was proved to have an insert in correct direction by digestion analysis using restriction enzymes, was selected (see FIG. 3). The plasmid obtained was named pRANG.

*E. coli* transformed with plasmid pRANG was named *Escherichia coli* HB101/pRANG, and it has been deposited to the National Institute of Bioscience and Human-Technology Agency of Industrial Science and Technology, under the accession number FERM BP-4949 since 28st Feb. 1994.

EXAMPLE 3

Expression of the Almond N-Glycosidase Polypeptide by Fission Yeast *Schizosaccharomyces pombe*

The uracil, leucine and adenine auxotroph *Schizosaccharomvces pombe* T-1 was transformed with the pRANG plasmid. The transformant was named *Schizpsaccharomyces pombe*/pRANG. Transformation was performed using 1 μg of plasmid pRANG by lithium acetate method of Okazaki et al. [Nucleic Acids Research, 18: 6485 (1990)]. A Leu$^+$ transformant was isolated, and the plasmid was identified. The transformant containing pRANG was named *Schizosaccharomvcespombe*/pRANG.

The *Schizosaccharomvces pombe*/pRANG cells were cultured in a minimal medium supplemented with thiamine, uracil and adenine [C. King et al., HANDBOOK OF GENETICS pp395–446 (1974) Prenum Press]. Cells grown to logarithmic growth phase were collected by centrifugation, and transferred to a minimal medium which was supplemented with uracil and adenine and did not contain thiamine. The cells were cultured to stationary phase. Cells were collected by centrifugation, and suspended in a acetate buffer solution for cell homogenization (containing 2 mM 4-(2-aminoethyl)benzenesulfonyl fluoride, 73 μM pepstatin A, 5 mM o-phenanthroline, and 5 mM EDTA). Glass beads (0.45 mm) were added, and cells were homogenated by vigorously stirring for 5 min with intermittent cooling. The homogenate was centrifuged, and the supernatant (the extract) was separated from the precipitate. Then, assay of N-glycosidase activity in the extract and the precipitate was performed using dabsyl ovomucoid glycopeptide as a substrate. The activity was found in the extract.

As described hereinabove, according to the present invention, the nucleotide sequence and the amino acid sequence of the almond N-glycosidase have been elucidated, whereby it is possible to provide an almond N-glycosidase gene. Thus, a genetic process advantageous industrially for preparing polypeptides having the almond N-glycosidase activity is provided. Similar N-glycodidase genes are also provided. In addition, on the basis of the nucleotide sequence of the almond N-glycosidase, probe DNAs and primers for PCR can be synthesized to obtain similar N-glycosidases using them. Further, on the basis of the amino acid sequence, antibodies can be prepared.

---

What is claimed is:

1. An isolated almond N-glycosidase gene encoding the amino acid sequence of SEQ ID NO:1.

2. The gene according to claim 1 comprising the DNA sequence of SEQ ID NO:2.

3. A recombinant vector comprising the gene according to claim 1.

4. A recombinant vector comprising the gene according to claim 2.

5. A process for preparing an almond N-glycosidase, which comprises culturing a recombinant microorganism transformed with the recombinant vector according to claim 3, and collecting the almond N-glycosidase from the culture.

6. The process according to claim 5, in which the recombinant microorganism is *Escherichia coli*.

7. The process according to claim 6, in which the recombinant microorganism is *Escherichia coli* HB101/pRANG (FERM BP-4949).

8. A process according to claim 5, in which the microorganism is a yeast.

9. A process according to claim 8, in which the microorganism is *Schizosaccharomyses pombe*.

10. A process for preparing an almond N-glycosidase, which comprises culturing a recombinant microorganism transformed with the recombinant vector according to claim 4, and collecting the almond N-glycosidase from the culture.

11. The process according to claim 10, in which the recombinant microorganism is *Escherichia coli*.

12. The process according to claim 11, in which the recombinant microorganism is *Escherichia coli* HB101/pRANG (FERM BP-4949).

13. A process according to claim 10, in which the microorganism is a yeast.

14. A process according to claim 13, in which the microorganism is *Schizosaccharomyses pombe*.

* * * * *